US 10,872,410 B2

United States Patent
Blanchard et al.

(10) Patent No.: US 10,872,410 B2
(45) Date of Patent: Dec. 22, 2020

(54) METHODS AND APPARATUS FOR ASSESSING IMMUNE SYSTEM ACTIVITY AND THERAPEUTIC EFFICACY

(71) Applicant: Animantis, LLC, San Diego, CA (US)

(72) Inventors: Martin Russell Blanchard, San Diego, CA (US); Ryan Stanley Kerwin, San Diego, CA (US); Bryan James Walker, Encinitas, CA (US)

(73) Assignee: ANIMANTIS, LLC, San Diego, CA (US)

(*) Notice: Subject to any disclaimer, the term of this patent is extended or adjusted under 35 U.S.C. 154(b) by 26 days.

(21) Appl. No.: 16/334,723

(22) PCT Filed: Sep. 21, 2017

(86) PCT No.: PCT/US2017/052689
§ 371 (c)(1),
(2) Date: Mar. 19, 2019

(87) PCT Pub. No.: WO2018/063914
PCT Pub. Date: Apr. 5, 2018

(65) Prior Publication Data
US 2019/0266723 A1 Aug. 29, 2019

Related U.S. Application Data

(60) Provisional application No. 62/401,631, filed on Sep. 29, 2016.

(51) Int. Cl.
*G06T 7/00* (2017.01)
*G01N 33/50* (2006.01)
*G06K 9/00* (2006.01)

(52) U.S. Cl.
CPC ....... *G06T 7/0012* (2013.01); *G01N 33/5026* (2013.01); *G01N 33/5029* (2013.01);
(Continued)

(58) Field of Classification Search
CPC ....... G06T 7/0012; G06T 7/11; G06T 7/0016; G06T 7/62; G06T 7/0014; G06T 7/136;
(Continued)

(56) References Cited

U.S. PATENT DOCUMENTS 4,886,655 A 12/1989 Griffin
5,460,945 A 10/1995 Springer
(Continued)

FOREIGN PATENT DOCUMENTS

WO WO 2016/132221 A2 8/2016

OTHER PUBLICATIONS

Abbassi O, Kishimoto TK, et al. "Eselectin supports neutrophil rolling in vitro under conditions of flow." *Journal of Clinical Investigations* 92(6): 2719-30. 1993.
(Continued)

*Primary Examiner* — Michael S Osinski
(74) *Attorney, Agent, or Firm* — Knobbe, Martens, Olson & Bear LLP

(57) ABSTRACT

Methods, compositions, and apparatuses are disclosed and described for assessing systemic immune response by monitoring changes of biophysical properties of mammalian immune cells or immune relevant bacterial cells in response to a gradient of chemoattractant in vitro.

24 Claims, 11 Drawing Sheets

(52) U.S. Cl.
CPC ....... *G06K 9/0014* (2013.01); *G06K 9/00147* (2013.01); *G01N 2800/7028* (2013.01); *G01N 2800/7095* (2013.01); *G06T 2207/20081* (2013.01); *G06T 2207/30024* (2013.01)

(58) Field of Classification Search
CPC ........... G06T 7/215; G06T 2207/30024; G06T 2207/20081; G06T 2207/30101; G06T 2207/10056; G06T 2207/10101; G06T 2207/30104; G01N 33/5029; G01N 33/5026; G01N 2800/7028; G01N 2800/7095; G01N 15/1475; G06K 9/0014; G06K 9/00147; G06K 9/00127; A61B 5/02007; A61B 6/481; A61B 6/504; A61B 8/0891; A61B 8/483; A61B 8/5223

See application file for complete search history.

(56) References Cited

U.S. PATENT DOCUMENTS

| | | | |
|---|---|---|---|
| 5,708,591 A | 1/1998 | Givens | |
| 6,101,449 A | 8/2000 | Givens | |
| 6,148,041 A | 11/2000 | Dent | |
| 6,238,874 B1 | 5/2001 | Jarnagin et al. | |
| 6,289,126 B1 | 9/2001 | Ishisaka | |
| 6,314,204 B1 | 11/2001 | Cham et al. | |
| 6,321,164 B1 | 11/2001 | Braun | |
| 6,716,588 B2 | 4/2004 | Sammak | |
| 6,898,532 B1 | 5/2005 | Toh | |
| 6,922,479 B2 | 7/2005 | Berliner | |
| 7,211,438 B2 | 5/2007 | Toh | |
| 7,585,640 B2 | 9/2009 | Ahearn | |
| 7,645,613 B2 | 1/2010 | Ivey | |
| 7,761,240 B2 | 7/2010 | Saidi | |
| 7,885,449 B2 | 2/2011 | Tafas | |
| 7,991,213 B2 | 8/2011 | Tafas | |
| 8,114,615 B2 | 2/2012 | Gough | |
| 8,385,625 B2 | 2/2013 | Tafas | |
| 8,425,843 B2 | 4/2013 | Ciotti | |
| 9,028,421 B2* | 5/2015 | Fujii | A61B 3/1233 600/504 |
| 9,076,198 B2* | 7/2015 | Yoshihara | G06K 9/0014 |
| 9,196,036 B2 | 11/2015 | Elter | |
| 10,712,331 B2* | 7/2020 | Little | G01N 21/6456 |
| 2003/0049851 A1 | 3/2003 | Toh | |
| 2006/0239533 A1 | 10/2006 | Tafas | |
| 2007/0092911 A1 | 4/2007 | Buechler | |
| 2009/0010512 A1* | 1/2009 | Zhu | G06T 5/50 382/130 |
| 2010/0034446 A1* | 2/2010 | Zhu | G06T 7/0014 382/130 |
| 2010/0054575 A1 | 3/2010 | Zhou | |
| 2010/0080439 A1 | 4/2010 | Karam et al. | |
| 2010/0098299 A1* | 4/2010 | Muquit | G06K 9/00013 382/115 |
| 2010/0216145 A1 | 8/2010 | Duvdevani | |
| 2011/0033102 A1* | 2/2011 | Zhu | G06T 7/0016 382/134 |
| 2013/0163845 A1 | 6/2013 | Tafas | |
| 2013/0315466 A1 | 11/2013 | Drell | |
| 2014/0030756 A1 | 1/2014 | Ramirez | |
| 2014/0099014 A1* | 4/2014 | Kii | G06T 7/62 382/133 |
| 2014/0139625 A1 | 5/2014 | Mathuis | |
| 2014/0369583 A1* | 12/2014 | Toji | A61B 8/06 382/131 |
| 2015/0257850 A1* | 9/2015 | Sakamoto | A61B 5/02007 600/424 |
| 2015/0299805 A1 | 10/2015 | Douvdevani | |
| 2015/0377905 A1 | 12/2015 | Burns | |
| 2016/0061824 A1 | 3/2016 | Hahn | |
| 2016/0258950 A1 | 9/2016 | Boilard | |
| 2017/0309018 A1* | 10/2017 | Shalev | G06T 7/0012 |
| 2017/0350805 A1* | 12/2017 | Murata | C12M 1/34 |
| 2018/0089496 A1* | 3/2018 | Molin | G06K 9/0014 |
| 2018/0236442 A1* | 8/2018 | Cox | B01L 3/5025 |
| 2018/0239949 A1* | 8/2018 | Chander | G06N 20/20 |
| 2019/0059840 A1* | 2/2019 | Fouras | G06T 7/11 |
| 2019/0274538 A1* | 9/2019 | Imamura | G06T 7/0016 |
| 2020/0232019 A1* | 7/2020 | Erber | G01N 33/57426 |

OTHER PUBLICATIONS

Attia UM, Marson S, and Alcock JR. "Micro-Injection Moulding of Polymer Microfluidic Devices." *Microfluidics and Nanofluidics* 7(1): 1-28. 2009.

Balk SH, Cha MY, et al. "Migration of neutrophils targeting amyloid plaques in Alzheimer's disease mouse model." *Neurobiology Aging* 35(6): 1286-1292. 2014.

Bar-Shalom Y, Daum F, and Huang J. "The probabilistic data association filter." *Control Systems IEEE* 29(6): 82-100. 2009.

Berhanu D, Mortari F, et al. "Optimized lymphocyte isolation methods for analysis of chemokine receptor expression." Journal of Immunological Methods 279(1): 199-207. 2003.

Brusca SB, Abramson SB, and Scher JU. "Microbiome and mucosal inflammation as extra-articular triggers for rheumatoid arthritis and autoimmunity." Current Opinion in Rheumatology 26(1): 101-107. 2014.

Burns AR, Bowden RA, et al. "P-selectin mediates neutrophil adhesion to endothelial cell borders." *Journal of Leukocyte Biology* 65: 299-306. 1999.

Capsoni F, Ongari AM, et al. "Effect of Efalizumab on neutrophil and monocyte functions in patients with psoriasis." *International Journal of Immunopathology and Pharmacology* 21(2): 437-45. 2008.

Clark RA, Kimball HR, and Decker JL. "Neutrophil chemotaxis in systemic lupus erythematosus." *Annals of the Rheumatic Diseases* 33: 167-72. 1974.

Corhay JL, Moermans C, et al. "Increased of exhaled breath condensate neutrophil chemotaxis in acute exacerbation of COPD." *Respiratory Research* 15(115): 1-11. 2014.

Croce M, Rigo, V, and Ferrini S. "IL-21: a pleiotropic cytokine with potential applications in oncology." Journal of Immunology Research 2015: 1-15. 2015.

Demaret J, Venet F, et al. "Marked alterations of neutrophil functions during sepsis-induced immunosuppression." *Journal of Leukocyte Biology* 98(6): 1081-90. 2015.

Eruslanov EB, Bhojnagarwala PS, et al. "Tumor-associated neutrophils stimulate T cell responses in early-stage human lung cancer." *Journal of Clinical Investigation* 124(12): 5466-80. 2014.

Feng D, Nagy JA, et al. Neutrophils Emigrate from Venules by a Transendothelial Cell Pathway in Response to FMLP. Journal of Experimental Medicine 187(6): 903-915. 1998.

Feng Y and Mrksich M. "The Synergy Peptide PHSRN and the Adhesion Peptide RGD Mediate Cell Adhesion through a Common Mechanism." *Biochemistry* 43: 15811-21. 2004.

Fournier BM and Parkos CA. "The role of neutrophils during intestinal inflammation." *Nature Review* 5(4): 354-66. 2012.

Freudenthal PS and Steinman RM. "The distinct surface of human blood dendritic cells, as observed after an improved isolation method." Proceedings of the National Academy of Sciences 87: 7698-7702. 1990.

Goncalves R and Mosser DM. "The isolation and characterization of murine macrophages." Current Protocols in Immunology 111(14): 1-14. 2015.

Gumbiner BM. "Cell Adhesion: The Molecular Basis of Tissue Architecture and Morphogenesis." Cell 84: 345-357. 1996.

Hartmann-Petersen et al. "Individual Cell Motility Studied by TirntJ-Lapse Video Recording: Influence of Experimental Conditions," Cytometry Pan A, Aug. 1, 2000 (Aug. 1, 2000), vol. 40. pp. 260-270.

Honda K and Littman DR. "The Microbiome in Infectious Disease and Inflammation." Annual Review of Immunology 30: 759-795. 2012.

(56) References Cited

OTHER PUBLICATIONS

Horvath S and Ritz BR. "Increased epigenetic age and granulocyte counts in the blood of Parkinson's disease patients." *Aging* 7(12): 1-13. 2015.

Kaplan MJ. "Neutrophils in the pathogenesis and manifestations of SLE." *National Review of Rheumatology* 7(12): 691-99. 2011.

Khan Z, Balch T, Dellart F. "An MCMCbased particle filter for tracking multiple interacting targets." *Computer Vision—ECCV 2004* 3024: 279-290. 2004.

Kilgore KS, Flory CM, et al. The membrane attack complex of complement induces interleukin-8 and monocyte chemoattractant protein-1 secretion from human umbilical vein endothelial cells. American Journal of Pathology 149(3): 953-961. 1996.

Kramer el al. "In Vitro Cell Migration and Invasion Assays," Mutation Research/Reviews in Mutation Research, Mar. 31, 2013 (Mar. 31, 2013), vol. 752, pp. 10-24. entire document.

Lammermann et al. "Rapid Leukocyte Migration by Integrin-Independent Flowing and Squeezing," Nature. May 1, 2008 (May 1, 2008), vol. 453, pp. 51-55. entire document.

Ley K. "Arrest Chemokines." *Frontiers in Immunology*. Editorial. 2014.

Luster AD, Alon R, and von Andrian UH. Immune cell migration in inflammation: present and future therapeutic targets. Nature Immunology 6: 1182-1190. 2005.

Mantovani A. "Macrophages, Neutrophils and Cancer: A Double Edged Sword." *New Journal of Science* Epub. 2014.

McEver RP and Cummings RD. "Role of PSGL-1 Binding to Selectins in Leukocyte Recruitment." Journal of Clinical Investigation 100(3): 485-492. 1997.

Miller NM, Wang J, et al. "Anti-inflammatory mechanisms of IFN-γ studied in experimental autoimmune encephalomyelitis reveal neutrophils as a potential target in multiple sclerosis." *Frontiers in Neuroscience* 1-13. 2015.

Oh H, Siano B, and Diamond S. "Neutrophil Isolation Protocol." *Journal of Visual Experiments* 17: 745. 2008.

Paschke S, Weidner AF, et al. "Inhibition of neutrophil chemotaxis by colchicine is modulated through viscoelastic properties of subcellular compartments." *Journal of Leukocyte Biology* 94: 1091-96. 2012.

Reichel CA, Rehberg M, et al. "Ccl2 and Ccl3 mediate neutrophil recruitment via induction of protein synthesis and generation of lipid mediators." *Arteriosclerosis, Thrombosis, and Vascular Biology* 29(11): 1787-93. 2009.

Rumble JM, Huber AK, et al. "Neutrophil-related factors as biomarkers in EAE and MS." *The Journal of Experimental Medicine* 212(1): 23-35. 2015.

Sadik CD, Kim ND, and Luster AD. "Neutrophils cascading their way to inflammation." *Trends in Immunology* 32(10): 452-60. 2011.

Seeger FH, Torsten T, et al. "Cell isolation procedures matter: a comparison of different isolation protocols of bone marrow mononuclear cells used for cell therapy in patients with acute myocardial infarction." European Heart Journal 28: 766-772. 2007.

Simmons SB, Liggitt D, and Goverman JM. "Cytokine-regulated neutrophil recruitment is required for brain but not spinal cord inflammation during EAE." *Journal of Immunology* 193(2): 555-563. 2014.

Smolen JE, Petersen TK, et al. "L-Selectin Signaling of Neutrophil Adhesion and Degranulation Involves p38 Mitogen-activated Protein Kinase." *Journal of Biological Chemistry* 275: 15876-84. 2000.

Terasawa T, Balk EM, et al. "Systematic Review: Comparative Effectiveness of Radiofrequency Catheter Ablation for Atrial Fibrillation." *Annals of Internal Medicine* 151(3): 191-202, 2009.

Trung PH, Prieur AM, and Griscelli C. "Neutrophil chemotaxis in juvenile chronic arthritis." *Annals of the Rheumatic Diseases* 39: 481-84. 1980.

Uzel G, Kleiner DE, et al. "Dysfunctional LAD-1 neutrophils and colitis." *Gastroenterology* 121(4): 958-64. 2001.

Vestweber D and Blanks JE. "Mechanisms that regulate the function of the selectins and their ligands." Physiological Reviews 79(1): 181-213. 1999.

Wagner JG and Roth RA. "Neutrophil migration during endotoxemia." *Journal of Leukocyte Biology* 66: 10-24. 1999.

Wang JM, Allavena CP, and Mantovani A. "Chemotactic activity of human recombinant granulocyte-macrophage colony-stimulating factor." *Immunology* 60: 439-444. 1987.

Wang JM, Chen ZG, et al. "Chemotactic activity of recombinant human granulocyte colony-stimulating factor." *Blood* 72: 1456-1460. 1988.

Wright HL, Moots RY, et al. "Neutrophil function in inflammation and inflammatory diseases." *Rheumatology* 49(9): 1618-31. 2010.

Wu J, Hillier C, et al. "A Microfluidic Platform for Evaluating Neutrophil Chemotaxis Induced by Sputum from COPD Patients." PLoS One 10(5):1-13. 2015.

Yan J, Kloecker G, et al. "Human polymorphonuclear neutrophils specifically recognize and kill cancerous cells." *OncoImmunology* 3(7): Epub. 2014.

Zhu X, Xiao L, et al. "Cyr61 is involved in neutrophil infiltration in joints by inducing IL-8 production by fibroblast-like synoviocytes in rheumatoid arthritis." *Arthritis Research & Therapy* 15(6): 187. 2013.

International Search Report and Written Opinion issued in PCT/US2017/052689, dated Dec. 12, 2017.

Search Report issued in EP application No. EP 17857229, dated Apr. 22, 2020.

\* cited by examiner

METHODS AND APPARATUS FOR ASSESSING IMMUNE SYSTEM ACTIVITY AND THERAPEUTIC EFFICACY

CROSS-REFERENCE TO RELATED APPLICATIONS

The present application is a U.S. National Phase Application under 35 U.S.C. § 371 of International Application No. PCT/US2017/052689, filed on Sep. 21, 2017, designating the United States of America and published in the English language on Apr. 5, 2018; which claims the benefit of priority to U.S. Provisional Patent Application No. 62/401,631, filed on Sep. 29, 2016. The content of each of these related applications is incorporated by reference herein in its entirety.

FIELD OF THE DISCLOSURE

A method and apparatus are disclosed for assessing immune responses in a human by in vitro evaluation of biophysical properties of mammalian immune cells or relevant bacterial cells. Quantification of the immune response includes biophysical assessment of the "crawling phase" of migratory cells.

BACKGROUND

During the initial immune response, white blood cells, or leukocytes, undergo a process in which they attach and arrest to the inner wall of blood vessels (Wright H L, Moots R Y, et al. "Neutrophil function in inflammation and inflammatory diseases." *Rheumatology* 49(9): 1618-31. 2010). Following this adhesion phase, cells begin to crawl, termed chemotaxis, toward a chemical gradient that signifies cellular gaps in the blood vessel wall through which leukocytes can transmigrate (Wright H L, Moots R Y, et al. "Neutrophil function in inflammation and inflammatory diseases." *Rheumatology* 49(9): 1618-31. 2010; Sadik C D, Kim N D, and Luster A D. "Neutrophils cascading their way to inflammation." *Trends in Immunology* 32(10): 452-60. 2011). However, many factors and diseases can disrupt this process, either causing the leukocytes to respond insufficiently or causing them to exhibit excessive immune response in the body (i.e. inflammation). When this occurs, various medical phenotypes result, ranging from mild symptoms, such as itching and swelling, to very severe effects, such as tissue scarring and organ failure (Kolaczkowska E and Kubes P. "Neutrophil recruitment and function in health and inflammation." *Nature Reviews Immunology* 13:159-75. 2013).

Paramount to treating and characterizing inflammation-mediated disease is the ability to properly gauge and mitigate levels of systemic immune response present in relevant mammalian samples. However, current methods of assessing inflammation are rudimentary, normally involving only the qualitative examination of resulting symptoms. Even the primary diagnostic assay to currently measure inflammation, the C-reactive protein test, lacks the specificity required to work across all patients, and only indicates the presence of inflammation at severe levels.

SUMMARY

In some embodiments is provided a device and methods for measuring an inflammatory response in a subject. In some embodiments is provided a device for measuring an inflammatory response in a subject. In some embodiments, the device includes an interior portion and an exterior portion. In some embodiments, the interior portion of the device includes a sample reservoir configured to receive a sample, an elongate channel, and a processing chamber. In some embodiments, the processing chamber is in fluid communication with the sample reservoir through the elongate channel.

In some embodiments, the elongate channel is approximately 1, 2, 3, 4, 5, 6, 7, 8, 9, or 10 cm in length, or within a range defined by any two of the aforementioned values. In some embodiments, the narrow channel includes a first end and a second end. In some embodiments, the first end of the channel includes the processing chamber to house a lyophilized pellet containing chemoattractive chemicals relevant to immune response. In some embodiments, the second end of the channel includes a first and a second small port. In some embodiments, the first port is an inlet and the second port is an outlet. In some embodiments, the first and second ports facilitate a rinse and a fill phase of the assay. In some embodiments, the outlet is located at the second end of the narrow channel opposite the processing chamber at the first end of the channel. In some embodiments, the outlet leads to a blister pack compartment that serves as a waste reservoir for assay rinse cycles. In some embodiments, the outlet's channel also contains a small external opening located above the path to the waste reservoir. In some embodiments, the external opening is specifically fitted to accept the nozzle tip of a vacuum system on board the automated analyzer. In some embodiments, the external opening coupled to a vacuum system serves to instigate vacuum-mediated flow of buffer across the cassette channel while keeping all waste material contained on the disposable cassette. In some embodiments, the inlet port leads to a blister pack compartment that serves as a buffer reservoir. In some embodiments, the inlet port is located approximately 0.1, 0.2, 0.3, 0.4, 0.5, 0.6, 0.7, 0.8, 0.9, 1, 1.1, 1.2, 1.3, 1.4, 1.5, 1.6, 1.7, 1. 8. 1.9, or 2 cm from the outlet port, or within a range defined by any two of the aforementioned values.

In some embodiments, the exterior dimensions of the device are approximately 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5 cm in length or within a range defined by any two of the aforementioned values. In some embodiments, the exterior dimensions of the device are approximately 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5 cm in width, or within a range defined by any two of the aforementioned values. In some embodiments, the exterior dimensions of the device are approximately 0.25, 0.5, 0.75, 1.0, 1.25, 1.5. 1.75, or 2.0 cm in height, or within a range defined by any two of the aforementioned values. In some embodiments, the devices are intended for single use and require no technical intervention following sample introduction.

In some embodiments, the sample reservoir includes one or more cell adhesion molecules and a chemoattractant. In some embodiments, the one or more cell adhesion molecules includes a peptide or a protein. In some embodiments, the one or more cell adhesion molecules includes one or more of a lectin, a laminin, a selectin, a fibronectin, a collagen, a fibrinogen, or a gelatin.

In some embodiments, the chemoattractant includes N-Formylmethionyl-leucyl-phenylalanine (fMLF), fMet, IL-8, Leukotrene B4, CXCL1, CXCL2, CXCL8, CXCL9, CXCL10, CXCL12, CCL2, CCL3, CCL5, CCL11, CCL19, CCL21, CX3CL1, C5a, C5b, G-CSF, GM-CSF, IL-1, IL-3, IL-4 IL-5, IL-6, IL-7, IL-11 IL-17, IL-21, IL-1β, TNFα, stem cell factor (SCF), thrombin, erythropoietin (EPO), IFN-α, IFN-β, IFN-γ and any combination thereof.

In some embodiments is provided a method for assessing an inflammatory response in a subject. In some embodiments, the method includes providing a device for measuring an inflammatory response in a subject. In some embodiments, the device is as described above, and includes a sample reservoir having one or more cell adhesion molecules and a chemoattractant and a processing chamber in fluid communication with the sample reservoir through an elongate channel. In some embodiments, the method includes applying a biological sample to the sample reservoir. In some embodiments, the biological sample includes one or more cells. In some embodiments, the method includes classifying the one or more cells by assessing one or more physical variables of the one or more cells. In some embodiments, the method includes comparing the one or more physical variables against physical parameters of known inflammatory conditions and thereby determining the inflammatory response of the subject.

In some embodiments, the one or more physical variables of the one or more cells includes cell morphology, cell position, cell directionality, cell orientation, cell perimeter, cell luminance, cell area, cell velocity, cell speed, cell acceleration, cell direction, cell circularity, cellular branching events, cell branch length, cell image moments (or Hu moments), cell eccentricity, cell path trends, cell spreading, cell grouping, neutrophil extracellular trap (NET) formations, degranulation events, or overall prevalence.

In some embodiments, the inflammatory response is a result of an immune response in the subject.

In some embodiments, the subject suffers from or is susceptible to cancer, atherosclerosis, sepsis, asthma, inflammatory bowel disease, chronic obstructive pulmonary disease, allergies, systemic lupus erythematosus, lupus nephritis, vasculitis, osteoarthritis, psoriatic arthritis, rheumatoid arthritis, ankylosing spondylitis, psoriasis, non-alcoholic fatty liver disease, cirrhosis, type I diabetes, type II diabetes, diabetes mellitus, multiple sclerosis, Alzheimer's disease, Parkinson's disease, cystic fibrosis, eosinophilic esophagitis, acute myocardial infarction, pneumonia, heart failure, hospital readmission following surgical procedure, idiopathic pulmonary fibrosis, organ transplant rejection and/or hospital readmission, implanted medical device rejection, or general immune system assessment.

In some embodiments is provided a method for assaying a cellular response between a cell and a chemoattractant. In some embodiments, the method includes disposing a sample comprising one or more cells to a substrate. In some embodiments, the substrate includes an adhesion molecule. In some embodiments, the adhesion molecule includes a peptide or a protein. In some embodiments, the adhesion molecule includes one or more of a lectin, a laminin, a selectin, a fibronectin, a collagen, a fibrinogen, or a gelatin. In some embodiments, the method includes capturing one or more cells on the substrate through binding of the cell to the adhesion molecule. In some embodiments, the method includes exposing the captured one or more cells to a chemoattractant. In some embodiments, the chemoattractant includes N-Formylmethionyl-leucyl-phenylalanine (fMLF), fMet, IL-8, Leukotrene B4, CXCL1, CXCL2, CXCL8, CXCL9, CXCL10, CXCL12, CCL2, CCL3, CCL5, CCL11, CCL19, CCL21, CX3CL1, C5a, C5b, G-CSF, GM-CSF, IL-1, IL-3, IL-4 IL-5, IL-6, IL-7, IL-11 IL-17, IL-21, IL-1β, TNFα, stem cell factor (SCF), thrombin, erythropoietin (EPO), IFN-α, IFN-β, IFN-γ and any combination thereof. In some embodiments, the method further includes analyzing the one or more cells for a chemoattractant response. In some embodiments, analyzing the one or more cells includes monitoring the cells for one or more physical variables of the one or more cells, including cell morphology, cell position, cell directionality, cell orientation, cell perimeter, cell luminance, cell area, cell velocity, cell speed, cell acceleration, cell direction, cell circularity, cellular branching events, cell branch length, cell image moments (or Hu moments), cell eccentricity, cell path trends, cell spreading, cell grouping, neutrophil extracellular trap (NET) formations, degranulation events, or overall prevalence.

In some embodiments is provided a method of classifying a cell. In some embodiments, the method includes combining the cell with a chemoattractant in a vessel having a first transparent portion. In some embodiments, the chemoattractant includes N-Formylmethionyl-leucyl-phenylalanine (fMLF), fMet, IL-8, Leukotrene B4, CXCL1, CXCL2, CXCL8, CXCL9, CXCL10, CXCL12, CCL2, CCL3, CCL5, CCL11, CCL19, CCL21, CX3CL1, C5a, C5b, G-CSF, GM-CSF, IL-1, IL-3, IL-4 IL-5, IL-6, IL-7, IL-11 IL-17, IL-21, IL-1β, TNFα, stem cell factor (SCF), thrombin, erythropoietin (EPO), IFN-α, IFN-β, IFN-γ and any combination thereof. In some embodiments, the method includes receiving a video including a plurality of images showing the cell through the first transparent portion. In some embodiments, for each image included in the plurality of images, the method includes identifying a set of locations within an image where the cell may be located using at least one of temporal variance in pixel values between images and pixel variance from a mean for the image. In some embodiments, the method includes generating a binary image for the image, the binary image indicating the set of locations. In some embodiments, for each binary image, the method includes generating a probability that each location in the set of locations is the location of the cell. In some embodiments, the method includes assigning one location from the set of locations for each binary image, wherein the assignment maximizes the probability for all of the binary images. In some embodiments, the method includes generating a set of metrics for the cell, the set of metrics generated using changes in location for the cell between binary images for sequentially captured images included in the video. In some embodiments, the method includes obtaining a classification model, the classification model receiving at least a portion of the set of metrics as an input and generating a classification as an output. In some embodiments, the method includes classifying the cell using the set of metrics and the classification model.

In some embodiments, the method further includes determining a hypothesis count based on at least one of a type for the cell and the chemoattractant. In some embodiments, the method includes obtaining a motion model for the cell, the motion model receiving at least a location of the cell in a first image as an input and generating a predicted location for the cell in a subsequent image as an output. In some embodiments, for each binary image, the method include generating a set of hypothetical locations for the cell using the motion model, wherein the size of the set of hypothetical locations corresponds to the hypothesis count, and assigning a score to each hypothetical location in the set of hypothetical locations based on a similarity calculated using a negative exponential Gaussian function of the Mean Squared Error (MSE) between the hypothetical location and a template image, wherein the probability that each location in the set of locations is the location of the cell is generated using the scores.

In some embodiments, the method further includes generating a random seed value for generating the probability for each location in the set of locations for each binary image. In some embodiments, the method includes storing the random seed value in a data storage device in association with an identifier for a source of the cell. In some embodiments, the method includes receiving a second video including a plurality of images showing a second cell from the source. In some embodiments, the method includes extracting a portion of an image included in the plurality of images, the portion indicating the identifier. In some embodiments, the method includes retrieving the random seed value from the data storage device using the identifier. In some embodiments, the method includes classifying the second cell using the random seed value.

In some embodiments, the set of metrics includes a metric indicating a characteristic of the cell shown in the image included in the plurality of images sequentially captured.

In some embodiments, the set of metrics includes a metric indicating a change in a characteristic of the cell between images included in the plurality of images sequentially captured.

In some embodiments, the characteristic of the cell includes cell area, cell velocity, direction of cell migration, cell speed, cell momentum, cell polarization, cell circularity, number of distinct protrusions from each cell, and all first order time-dependent derivatives thereof.

In some embodiments, the plurality of images comprises at least 180 images, and wherein each of the plurality of images further show between 1 and 299 other cells through the first transparent portion.

In some embodiments, is provided a method of classifying a cell. In some embodiments, the method includes receiving a video including a plurality of images showing the cell. In some embodiments, the method includes generating a binary image for each image included in the plurality of images, individual binary image indicating a set of locations within the respective image where the cell may be located. In some embodiments, for each binary image, the method includes generating a probability that each location in the set of locations is the location of the cell. In some embodiments, the method includes assigning one location from the set of locations for each binary image, wherein the assignment maximizes the probability for all of the binary images. In some embodiments, the method includes generating a set of metrics for the cell, the set of metrics generated using changes in a characteristic for the cell between binary images for sequentially captured images included in the video. In some embodiments, the method includes classifying the cell using the set of metrics and a classification model, the classification model receiving at least a portion of the set of metrics as an input and generating a classification as an output.

In some embodiments is provided a method for determining the characteristics of one or more cells. In some embodiments the method includes dynamically measuring one or more physical variables of one or more cells when introduced to a biomimetic environment. In some embodiments the method includes applying one or more measured variables to calculate quantifiable metrics relevant to each cell, wherein one or more calculated metrics relates to the physical characteristics of each cell, the motility of each cell, or the inflammatory potential of each cell.

In some embodiments, the one or more cells is selected from the group of cells relevant to macroscopic inflammatory behavior, including neutrophils, basophils, eosinophils, natural killer cells, mast cells, platelets, Kupffer cells, macrophages, B cells, T cells, dendritic cells, stem cells, progenitor cells, bacterial cells, or circulating tumor cells, or combinations thereof.

In some embodiments, the biomimetic environment for cellular introduction comprises one or more peptides, proteins, or chemicals.

In some embodiments, the proteins and peptides includes one or more of collagen I, collagen IV, fibronectin, p-selectin, 1-selectin, e-selectin, laminin, fibrinogen, and gelatin.

In some embodiments, the chemicals are comprised of one or more relevant immuno-modulatory chemicals, including N-Formylmethionyl-leucyl-phenylalanine (fMLF), fMet, IL-8, Leukotrene B4, CXCL1, CXCL2, CXCL8, CXCL9, CXCL10, CXCL12, CCL2, CCL3, CCL5, CCL11, CCL19, CCL21, CX3CL1, C5a, C5b, G-CSF, GM-CSF, IL-1, IL-3, IL-4 IL-5, IL-6, IL-7, IL-11 IL-17, IL-21, IL-1$\beta$, TNF$\alpha$, stem cell factor (SCF), thrombin, erythropoietin (EPO), IFN-$\alpha$, IFN-$\beta$, IFN-$\gamma$ and any combination thereof.

In some embodiments, the one or more measured variables and quantified metrics include cell area, cell velocity, direction of cell migration, cell speed, cell momentum, cell polarization, cell circularity, number of distinct protrusions from each cell, and all first order time-dependent derivatives thereof.

In some embodiments, the one or more metrics of two or more cells are compared and contrasted to determine degree of sample heterogeneity and aggregated and averaged to determine variables and metrics representative of total sample populations.

In some embodiments, the sample heterogeneity among two or more cells and averaged biophysical values are assessed and weighted to determine the overall degree of inflammatory potential present in a sample.

In some embodiments is provided a system for assessing one or more properties of cell samples. In some embodiments, the system includes a medical device for containing and staging samples consisting of one or more relevant cells, a corresponding hardware device to acquire computerized images for analysis, and an image processing system for measuring one or more physical variables of one or more cells.

In some embodiments is provided a medical device. In some embodiments, the medical device is a disposable biomimetic cassette that consists of an elongated internal geometry to facilitate the adhesion of one or more cells at one end and the gradual diffusion of chemicals placed on the opposite end.

In some embodiments, the biomimetic cassette includes an on-board container to house cell-suitable buffer or media with an opening to the cassette's inner chamber to facilitate assay rinsing and fill cycles. In some embodiments, the biomimetic cassette includes a connected on-board expandable container for the collection of sample waste. In some embodiments, the biomimetic cassette includes a nozzle port to facilitate the vacuum-mediated transfer of liquid from buffer container to inner channel and from inner channel to waste container.

In some embodiments is provided a microscopy and image acquisition device specific to the dimensions of the medical device described herein, and designed to acquire data from inputted samples in the form of one or more computerized images.

In some embodiments, the image acquisition device includes a phase-contrast microscopy setup located above the area of sample placement, a camera attachment to produce and temporarily save one or more digital images per assay, a vacuum system to instigate assay phases inside the medical device, a digital logic board interface for the input of desired acquisition settings, and an Ethernet port connection to internet access, through which acquired data is sent to centralized servers for automated analysis.

In some embodiments is provided an image processing system for the direct measurement of variables indicated by acquired sample images and the calculation of additional metrics from those measured variables, as well as the interpretation of those variables and metrics based on data acquired from previous samples.

In some embodiments, the an image processing system links two or more images of the same sample to produce a single time-lapse video file representative of an entire assay, tracks each cell present in a sample from frame to frame of the produced video and measures relevant variables at each frame, calculates additional metrics of each cell at each frame from these directly measured variables, compares and contrasts variables and metrics corresponding to two or more cells in a given sample to assess sample heterogeneity, and utilizes trained and untrained machine learning analysis to assess the behavior of cells in a given sample to those expressed by cells contained in each previous relevant sample.

DETAILED DESCRIPTION

Figure 1:
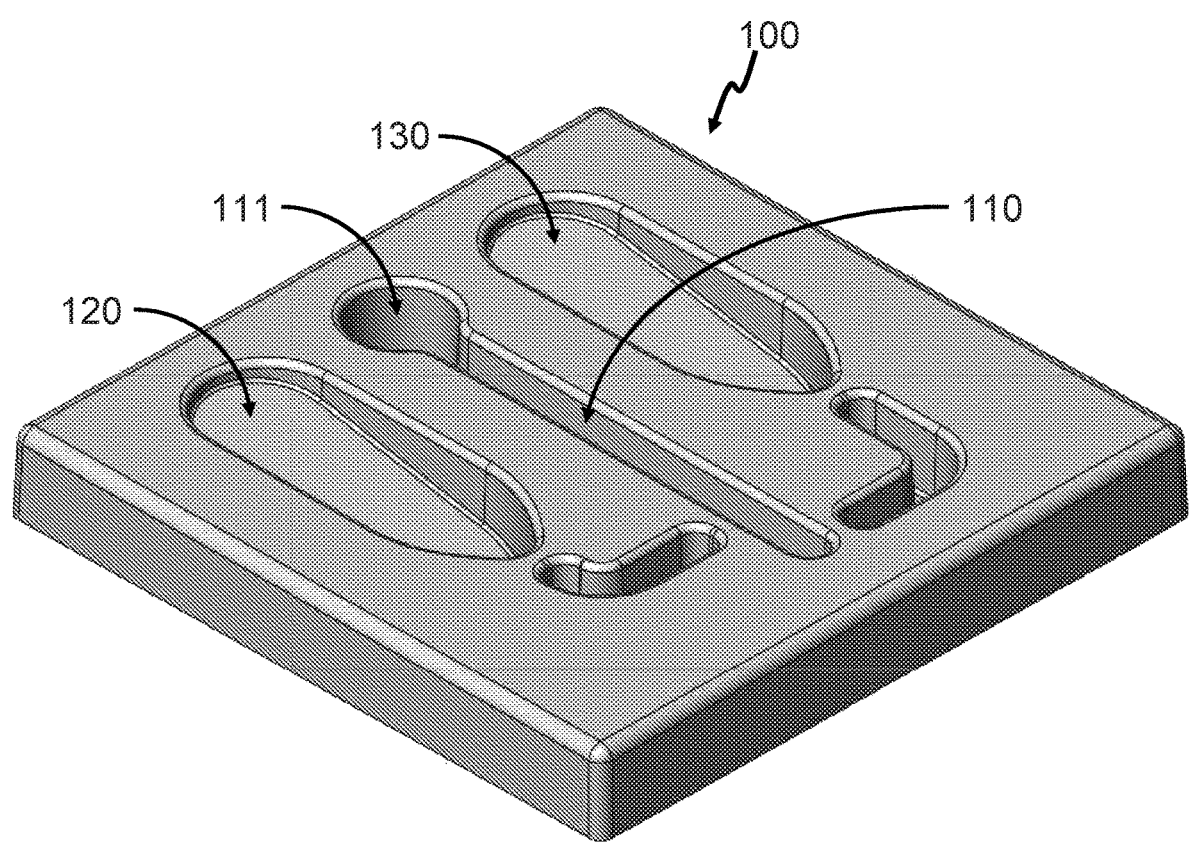
FIG. 1 is a perspective view of a chemotaxis cassette according to an example implementation.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Current methods of assessing inflammation in a subject are rudimentary, normally involving only the qualitative examination of resulting symptoms. Even the primary diagnostic assay to currently measure inflammation, the C-reactive protein test, lacks the specificity required to work across all patients, and only indicates the presence of inflammation at severe levels. To fill this critical need, a new kind of point-of-care clinical assay is disclosed herein that uses cell chemotaxis as a means of assessing present inflammation in a subject.

The immune cell behavior predominantly relevant to the technology herein, specifically the "crawling phase of primary neutrophils," has been demonstrated in vitro (Lokuta M A, Nuzzi P, and Huttenlocher A. "Analysis of neutrophil polarization and chemotaxis." *Methods in Molecular Biology* 412: 211-29. 2007). Additionally these cells often are found to exhibit different crawling behavior when originating from inflamed environments (Sadik C D, Kim N D, and Luster A D. "Neutrophils cascading their way to inflammation." *Trends in Immunology* 32(10): 452-60. 2011; Kolaczkowska E and Kubes P. "Neutrophil recruitment and function in health and inflammation." *Nature Reviews Immunology* 13:159-75. 2013). However, certain barriers have prevented the reliable quantification of such in vitro behavior, mostly notably the inability to measure the changes in any statistically significant way due to sample variability. In light of this problem, an image processing system capable of measuring small cellular changes with a high degree of accuracy is described. Methods and algorithms disclosed automate the process of cross-assay comparisons, identifying, and then assessing, the most statistically significant differences in behavior among cells isolation from healthy subjects compared to symptomatic subjects. This new cell phenotyping platform for gauging the state of immune microenvironments can be applied to migratory monocytes, such as macrophages and Kupffer cells, migratory lymphocytes, including T cells, B cells, and natural killer (NK) cells, and granulocytes, including neutrophils, basophils, and eosinophils, as well as other migratory cells of interest including dendritic cells, platelets, circulating tumor cells, stem cells, progenitor cells, and bacterial cells (Brusca S B, Abramson S B, and Scher J U. "Microbiome and mucosal inflammation as extra-articular triggers for rheumatoid arthritis and autoimmunity." Current Opinion in Rheumatology 26(1): 101-107. 2014; Honda K and Littman D R. "The Microbiome in Infectious Disease and Inflammation." Annual Review of Immunology 30: 759-795. 2012).

Disclosed herein is a method for assessing inflammatory responses in subjects by in vitro evaluation of biophysical properties of leukocytes or bacteria isolated from primary samples. In some embodiments, the method exposes isolated cells of interest to chemoattractants in vitro in amounts sufficient to induce changes in cellular behavior. In some embodiments, the changes of biophysical properties of the isolated cells are recorded. In some embodiments, the changes of biophysical properties of the isolated cells include, for example, cell morphology, cell position, cell directionality, cell orientation, cell perimeter, cell luminance, cell area, cell velocity, cell speed, cell acceleration, cell direction, cell circularity, cellular branching events, cell branch length, cell image moments (or Hu moments), cell eccentricity, cell path trends, cell spreading, cell grouping, neutrophil extracellular trap (NET) formations, degranulation events, or overall prevalence. In some embodiments, the cell characteristics includes one or more of cell area, cell velocity, direction of cell migration, cell speed, cell momentum, cell polarization, cell circularity, number of distinct protrusions from each cell, and all first order time-dependent derivatives thereof.

More specifically, in vitro changes in biophysical properties of the cells are monitored by time-lapse microscopy over time, and data are collected, at predetermined time intervals in an automated manner. The data are then compared with data collected from samples afflicted known inflammatory conditions, and with healthy sample phenotypes, using the same parameters, to determine the degree of immune response in the target sample. Available reference data may be used instead of or in addition to healthy sample comparisons acquired via the method described herein for the purpose of statistical training, including genetic data, proteomic data, patient questionnaires, clinical outcomes, pathology findings, and expert opinion. Data collection and comparison are performed by customized image processing system detailed below. In addition, application of the method described herein may be used to monitor change in immune response in a single subject at multiple time points.

As used herein, the term "physical properties" or "biophysical properties" in reference to the characteristics of a cell refers to at least one of cell morphology, cell position, cell directionality, cell orientation, cell perimeter, cell luminance, cell area, cell velocity, cell speed, cell acceleration, cell direction, cell circularity, cellular branching events, cell branch length, cell image moments (or Hu moments), cell eccentricity, cell path trends, cell spreading, cell grouping, neutrophil extracellular trap (NET) formations, degranulation events, or overall prevalence of the cell being analyzed. In some embodiments, the characteristics of the cell includes one or more of cell area, cell velocity, direction of cell migration, cell speed, cell momentum, cell polarization, cell circularity, number of distinct protrusions from each cell, and all first order time-dependent derivatives thereof.

In some embodiments is provided a device for measuring an inflammatory response in a subject. As used herein, the device is designed for receiving a sample and for isolating cells to monitor and analyze changes in the biophysical properties of the isolated cells. Changes of biophysical properties of the isolated cells include, for example, cell morphology, cell position, cell directionality, cell orientation, cell perimeter, cell luminance, cell area, cell velocity, cell speed, cell acceleration, cell direction, cell circularity, cellular branching events, cell branch length, cell image moments (or Hu moments), cell eccentricity, cell path trends, cell spreading, cell grouping, neutrophil extracellular trap (NET) formations, degranulation events, or overall prevalence. In some embodiments, the device is termed a "chemotaxis cassette." As used herein, the term "cassette" is not to be defined by any particular housing or structure, but any suitable housing or structure for analyzing characteristics of the isolated cells. In some embodiments, the cassette may be disposable, such as a one-time use cassette. In some embodiments, the cassette may be reusable.

In some embodiments, the cassette includes a reservoir, channel, well, or deposition site for depositing a sample. In some embodiments, the reservoir is configured to receive a sample. In some embodiments, the reservoir includes one or more cell adhesion molecules and a chemoattractant. In some embodiments, the cassette includes an elongate channel, and a processing chamber. In some embodiments, the processing chamber is in fluid communication with the sample reservoir through the elongate channel. In some embodiments, the cassette includes a buffer well and a waste well. In some embodiments, the buffer well includes a buffer, such as, for example Dulbecco's phosphate buffered saline (DPBS). In some embodiments, the cassette includes a field of view, configured for viewing cells to monitor and analyze characteristics of the cell.

In an embodiment, a whole blood sample is obtained from a subject and is introduced into one end of a chemotaxis cassette. Over the course of a brief incubation period, immune-relevant cells in the sample adhere to the surface of the chamber via protein-mediated arrest and a series of gentle rinse steps are used to remove peripheral cells from the field of view (e.g. red blood cells). In some embodiments, the surface of the chemotaxis cassette is functionalized with P-selectin to facilitate granulocyte adhesion. In some embodiments, other proteins could be used for this purpose, either standalone or complementary, including, for example, fibronectin (types collagen (types I-IV), fibrinogen, gelatin, E-selectin and L-selectin (Yoon P S, Boxer L A, et al. "Human neutrophil laminin receptors: activation-dependent receptor expression." *Journal of Immunology* 138(1): 259-65. 1987; Burns A R, Bowden R A, et al. "P-selectin mediates neutrophil adhesion to endothelial cell borders." *Journal of Leukocyte Biology* 65: 299-306. 1999; Feng Y and Mrksich M. "The Synergy Peptide PHSRN and the Adhesion Peptide RGD Mediate Cell Adhesion through a Common Mechanism." *Biochemistry* 43: 15811-21. 2004; Abbassi O, Kishimoto T K, et al. "E-selectin supports neutrophil rolling in vitro under conditions of flow." *Journal of Clinical Investigations* 92(6): 2719-30. 1993; Smolen J E, Petersen T K, et al. "L-Selectin Signaling of Neutrophil Adhesion and Degranulation Involves p38 Mitogen-activated Protein Kinase." *Journal of Biological Chemistry* 275: 15876-84. 2000). Optimal protein functionalization depends greatly on size of working samples and which cell types are of interest, making it vital that functionalization materials are modular. Thereafter, the cassette is filled with Dulbecco's phosphate buffered saline (DPBS), which serves to dissolve a lyophilized pellet containing relevant chemoattractants located at a distant location in the same chamber. This process results in a chemogradient that instigates immune response (i.e. directional crawling) in the sample primary cells. Changes in the biophysical properties of the cells in this environment within the chamber are tracked via time-lapse phase-contrast microscopy carried out by a specialized analyzer detailed below. The acquired data are compared against the data collections from subjects with known inflammatory and healthy phenotypes to find the overall best match for cell behavior. By this method, the level of immune response present in the blood sample is quantitatively assessed. In turn, this result serves as a measure of a subject's inflammatory status in vivo. These data sets are acquired through the utilization of unique computer vision algorithms designed to consistently detect and compare biophysical differences across measured cell samples not evident to qualitative analysis.

Methods of Cell Isolation

In some embodiments, granulocytes are obtained from a subject through the application of protein-mediated arrest. In some embodiments, standard spring-loaded lancets and capillary tubes are used to collect approximately a sample of patient blood and transfer the sample to the chemotaxis cassette described herein. In some embodiments, the sample has a volume of 10, 20, 30, 40, 50, 60, 70, 80, 90, or 100 µL or within a range defined by any two of the aforementioned volumes. In some embodiments, the cassette is functionalized with proteins that facilitate proper arrest and motility. In some embodiments, after the sample contacts the cassette, the cassette is inserted inside an analyzer. In some embodiments, the sample is diluted to a final dilution of 4 parts DPBS to 1 part whole blood to a final volume of approximately 50 μL. In some embodiments, the diluted sample is left on the chamber surface for approximately 5 minutes to allow for the protein-mediated capture of cells of interest. In some embodiments, following this passive incubation step, the analyzer instigates a gentle vacuum-mediated rinse phase, wherein DPBS is drawn from a blister pack located on the cassette. In some embodiments, 1 mL-2 mL of rinse solution is drawn across the cassette surface over the course of approximately 30 seconds to remove unbound cells, serum, and cellular debris. The process results in a field of view composed principally of cells of interest, specifically granulocytes, adhered to the cassette surface and primed for analysis. The process stated above, including incubation times, dilution ratios, and methods of cell capture, can be modified to fit specific experiment goals and parameters.

As an alternative to the granulocyte isolation process described above, the platform can also be applied to cell samples manually isolated from whole blood in advance, which might prove advantageous to specific experiments where sample purity is paramount. In such cases, the following density-mediated granulocyte isolation protocol is recommended, though variations can be applied to alter desired sample outcomes. This would additionally be suitable for well-established lymphocyte, monocyte, or bacterial isolation protocols (Oh H, Siano B, and Diamond S. "Neutrophil Isolation Protocol." *Journal of Visual Experiments* 17: 745. 2008; Berhanu D, Mortari F, et al. "Optimized lymphocyte isolation methods for analysis of chemokine receptor expression." Journal of Immunological Methods 279(1): 199-207. 2003; Freudenthal P S and Steinman R M. "The distinct surface of human blood dendritic cells, as observed after an improved isolation method." Proceedings of the National Academy of Sciences 87: 7698-7702. 1990; Goncalves R and Mosser D M. "The isolation and characterization of murine macrophages." Current Protocols in Immunology 111(14): 1-14. 2015; Seeger F H, Torsten T, et al. "Cell isolation procedures matter: a comparison of different isolation protocols of bone marrow mononuclear cells used for cell therapy in patients with acute myocardial infarction." European Heart Journal 28: 766-772. 2007; each of which is herein incorporated by reference in its entirety).

Accordingly, in some embodiments is provided a method analyzing cell samples that have been manually isolated. In some embodiments, granulocytes are obtained from a human subject (patient) by well-known blood separation protocols (Oh H, Siano B, and Diamond S. "Neutrophil Isolation Protocol." *Journal of Visual Experiments* 17: 745. 2008; incorporated herein by reference in its entirety). Typically, an individual has 3.8 mL of blood drawn by certified phlebotomists into a 5 mL syringe containing chemical agents to prevent coagulation and facilitate red blood cell (RBC) sedimentation. In particular, 0.7 mL of citrate-phosphate dextrose (CPD) and 0.5 mL of dextran are included to prevent coagulation, making for a total sample volume of 5 mL. Following the initial draw and passive sedimentation step, which takes approximately 1 hour at room temperature, the top yellow portion of the total sample is extracted from the syringe, while the bottom red layer is discarded. The collected portion is centrifuged at 1200 RPM for 6 minutes. Next, the supernatant is removed and the resulting pellet is resuspended in 5 mL of DPBS.

In some embodiments, following resuspension, 5 mL of histopaque is aliquoted into a 15 mL conical vial and the resuspended cell solution is pipetted on top of the histopaque, slowly so as to minimize mixing. In some embodiments, the sample is then centrifuged at 1200 RPM for 20 minutes in order to pull the sample through the histopaque, further separating the sample. In some embodiments, the supernatant is removed following centrifugation, and the resulting cell pellet is once more suspended in 5 mL of DPBS and centrifuged at 1200 RPM for 6 minutes. In some embodiments, the supernatant from the final centrifugation step is removed and the resulting pellet is suspended in 2% glucose-DPBS to a volume that gives desired cell density. In some embodiments, glucose is added to the final sample to increase the duration of cell viability, making for more reliable assays. In some embodiments, the final sample will contain approximately 8 million granulocytes in total, though this may vary significantly on a patient-to-patient basis. In some embodiments, the final sample cells are first suspended to a high concentration, counted by means of hemocytometer or electronic cell counter, and diluted to a desired final concentration. It should additionally be noted that all centrifugation times and speeds are adjustable within certain ranges to yield similar results according to standard practice within the knowledge of a person skilled in the art (Oh H, Siano B, and Diamond S. "Neutrophil Isolation Protocol." *Journal of Visual Experiments* 17: 745. 2008; incorporated herein by reference in its entirety).

Chemotaxis Induction Cassette

In some embodiments, is provided a method for the manufacture of a chemotaxis cassette. In some embodiments, the chemotaxis cassette includes one or more substrates. In some embodiments, the one or more substrates are functionalized with physiologically relevant proteins, which include, for example, collagen, fibronectin, and p-selectin. In some embodiments, the one or more substrates are cast into a plastic mold suitable for injection and observation of the sample immune-relevant cells (Attia U M, Marson S, and Alcock J R. "Micro-Injection Moulding of Polymer Microfluidic Devices." *Microfluidics and Nanofluidics* 7(1): 1-28. 2009; incorporated herein by reference in its entirety).

Figure 2A:
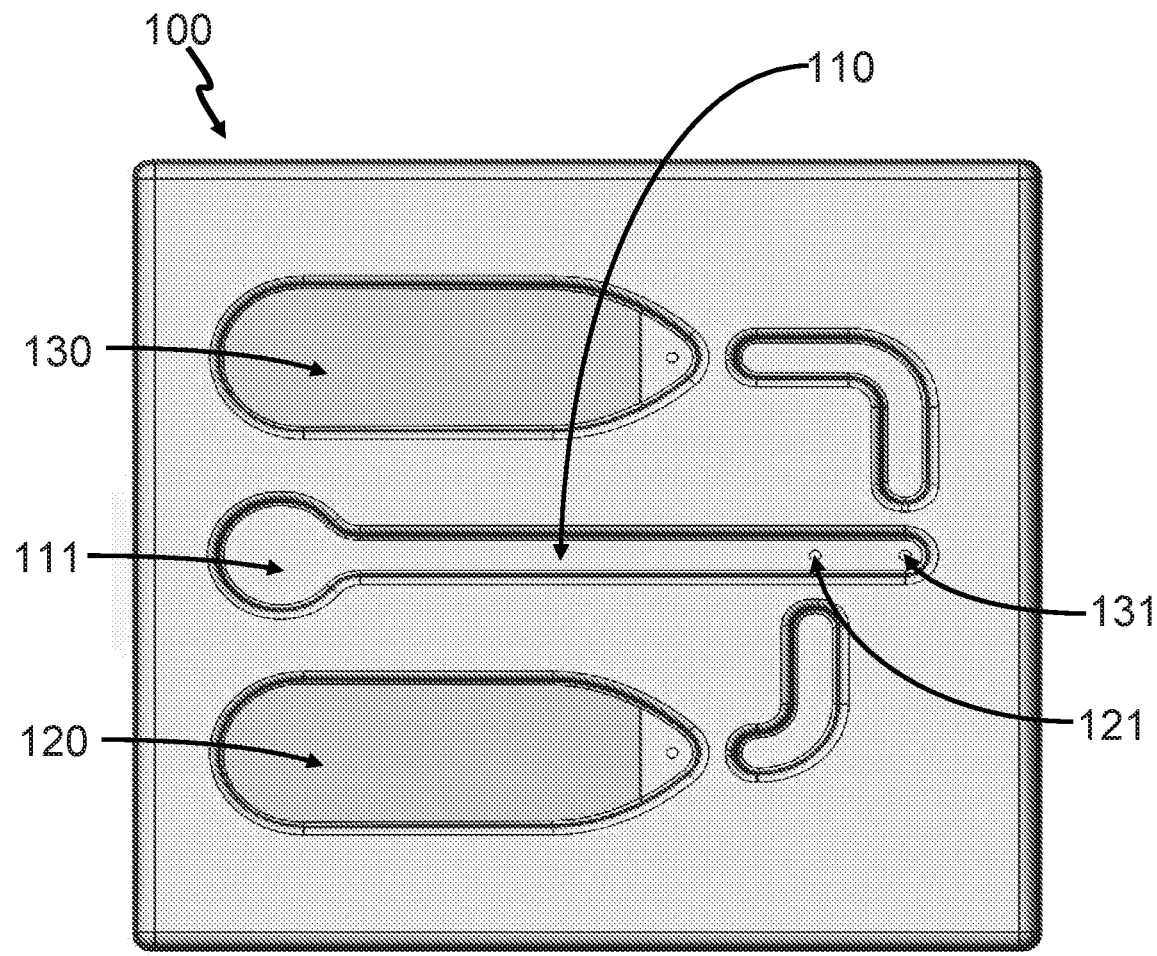
FIGS. 2A and 2B depict a top (FIG. 2A) and a bottom (FIG. 2B) view of one embodiment of a chemotaxis cassette.
Figure 2B:
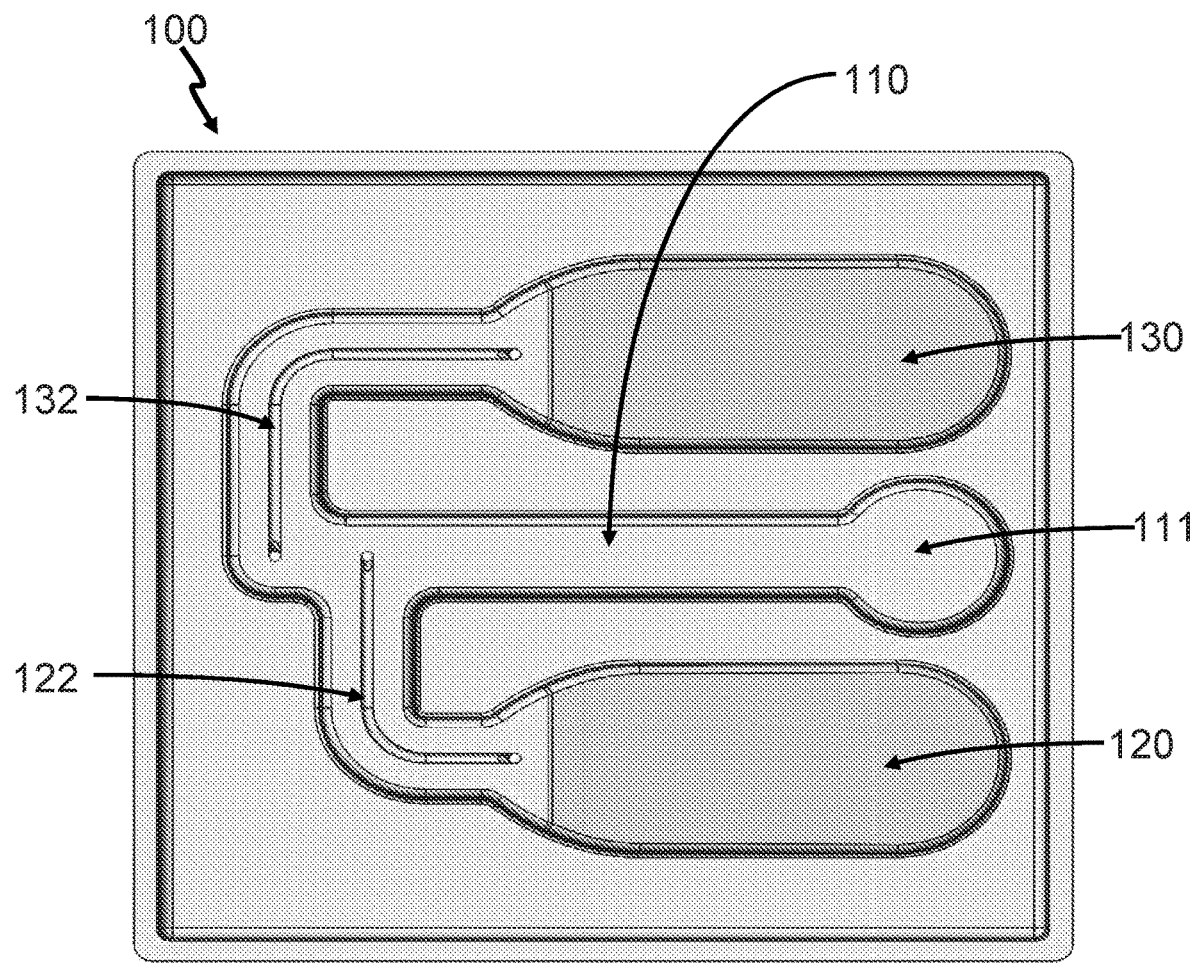

Referring now to FIG. 1 and FIGS. 2A and 2B, in some embodiments, the cassette 100 includes an interior portion. In some embodiments, the interior portion of the cassette includes an elongate channel 110. In some embodiments, the elongate channel is approximately 1, 2, 3, 4, 5, 6, 7, 8, 9, or 10 cm in length, or within a range defined by any two of the aforementioned values. In some embodiments, the elongate channel includes a first end and a second end. In some embodiments, the first end of the channel includes a processing chamber 111 to house a lyophilized pellet containing chemoattractive chemicals relevant to immune response. In some embodiments, the second end of the channel includes a first 121 and a second 131 small port. In some embodiments, the first port 121 is an inlet and the second port 131 is an outlet. In some embodiments, the first and second ports facilitate the rinse and fill phases of the assay. In some embodiments, the outlet is located at the second end of the narrow channel opposite the processing chamber at the first end of the channel. In some embodiments, the outlet leads to a blister pack compartment that serves as a waste reservoir 130 for assay rinse cycles. In some embodiments, the outlet's channel also contains a small external opening strategically located above the path to the waste reservoir. In some embodiments, the external opening is specifically fitted to accept the nozzle tip of a vacuum system on board the automated analyzer (described below). In some embodiments, the external opening coupled to a vacuum system serves to instigate vacuum-mediated flow of buffer across the cassette channel while keeping all waste material contained on the disposable cassette, where waste flows through the vacuum channel 132. In some embodiments, the inlet port 121 leads to a blister pack compartment that serves as a buffer reservoir 120. Buffer flows through the buffer channel 122, from the buffer reservoir 120 to the processing chamber 111. In some embodiments, the inlet port is located approximately 0.1, 0.2, 0.3, 0.4, 0.5, 0.6, 0.7, 0.8, 0.9, 1, 1.1, 1.2, 1.3, 1.4, 1.5, 1.6, 1.7, 1. 8. 1.9, or 2 cm from the outlet port, or within a range defined by any two of the aforementioned values. In some embodiments, this separation of the inlet and outlet port ensures that all biohazardous waste remains inside the cassette throughout the entire process, and can be readily discarded at the assay's conclusion.

In some embodiments, the exterior dimensions of a fully assembled cassette 100 are approximately 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5 cm in length or within a range defined by any two of the aforementioned values. In some embodiments, the exterior dimensions of a fully assembled cassette are approximately 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5 cm in width, or within a range defined by any two of the aforementioned values. In some embodiments, the exterior dimensions of a fully assembled cassette are approximately 0.25, 0.5, 0.75, 1.0, 1.25, 1.5. 1.75, or 2.0 cm in height, or within a range defined by any two of the aforementioned values. In some embodiments, the devices are intended for single use and require no technical intervention following sample introduction.

In some embodiments, the interior bottom surface of the chemotaxis cassette is functionalized with collagen I, fibronectin I, and P-selectin. In some embodiments, the concentration of collagen I, fibronectin I, and P-selectin is 0.1 mg/mL, 0.01 mg/mL, and 0.005 mg/mL, respectively. In some embodiments, the concentrations of the collagen I, fibronectin I, and P-selectin is 0.001, 0.002, 0.003, 0.003, 0.004, 0.005, 0.006, 0.007, 0.008, 0.009, 0.01, 0.02, 0.03, 0. 04, 0.05, 0.06, 0.07, 0.08, 0.09, 0.1, 0.2, 0.3, 0.4, 0.5 mg/mL or greater, or within a range defined by any two of the aforementioned values. In some embodiments, a water-based solution containing relevant proteins at the aforementioned concentrations is deposited on the cassette surface and is allowed to incubate passively for 30-60 minutes. In some embodiments, after the incubation step, the protein solution is aspirated and the cassette is allowed to dry before moving forward in the manufacturing process. In some embodiments, following the drying step, the interior walls of the cassette are coated with heparin, which serves as an anti-coagulant to ease the removal of red blood cells. It should be noted that while these concentrations and compositions are standardized for the sake of consistent assay comparison, they can be modulated to fit the needs of any given experiment.

In some embodiments, once the cassette is fully functionalized and the chemical pellet is inserted, the buffer and waste blister packs are attached and a lid is adhered. In some embodiments, the inlet blister pack is filled with approximately 3 mL of DPBS. In some embodiments, the outlet pack remains empty to allow for the collection of waste. In some embodiments, the cassette lid includes a single small opening above the narrow channel. In some embodiments, the single opening on the cassette lid is located approximately halfway between the inlet and outlet ports at the cassette base. In some embodiments, the opening on the lid is intended for sample introduction. In some embodiments, the small opening on the lid is sealed immediately following insertion of blood to allow for vacuum-mediated rinse and fill cycles. In some embodiments, to facilitate the uniform flow of fluid and prevent the formation of bubbles, hydrophobic vents, which allow for passage of air but not fluid, may be incorporated into a finalized cassette.

Automated Chemotaxis Analyzer

In order to ensure consistency and remove potential sources of user error, in some embodiments, the platform provided herein utilizes a custom analyzer tailored specifically to conduct the assay process detailed herein. In some embodiments, the principal components of the analyzer include one or more of: a tray designed to hold the cassette described above, a vacuum system to pull buffer from one blister pack to another and instigate rinse and fill phases, phase-contrast microscopy equipment to view and record cells including light source and camera attachment, a user interface, and secure internet connectivity to communicate with an offsite server.

In some embodiments, the tray of the analyzer includes a slot. In some embodiments, the slot is shaped to uniquely fit the cassette. In some embodiments, the slot includes asymmetric divots to minimize the possibility of incorrect cassette placement. In some embodiments, the tray is ejected using a button located at the front of the analyzer. In some embodiments, a sample-loaded cassette is placed into its corresponding slot. In some embodiments, the same button is pressed once more to close the tray. In some embodiments, a different button is pressed to close the tray.

In some embodiments, the analyzer includes microscopy equipment. In some embodiments, once inserted, the cassette is positioned directly above the analyzer's microscopy equipment. In some embodiments, the microscopy equipment is focused on the approximate site of sample introduction. In some embodiments, for purposes of consistency and reproducibility, focus and light intensity are set to default values, as are exposure settings for picture acquisition.

In some embodiments, once the cassette is in place inside the analyzer, a nozzle tip moved by a motorized arm is positioned at the external opening of the outlet's channel, creating an airtight seal. In some embodiments, following the seal, a vacuum pump attached to the nozzle tip is briefly activated to draw DPBS into the cassette channel to mix with the blood sample. In some embodiments, the vacuum draws approximately 10, 20, 30, 40, 50, 60, 70, 80, 90 or 100 µL of DPBS, or greater, or a volume within any two of the aforementioned values. In some embodiments, the mixture of DPBS and sample is passively incubated to allow for adequate cell adhesion. In some embodiments, the sample is incubated for 1, 2, 3, 4, 5, 6, 7, 8, 9, or 10 minutes, for a time within any two of the aforementioned values. In some embodiments, following the incubation, the vacuum system is reactivated to induce a gentle rinse step. In some embodiments, the rinse step uses approximately 1-2 mL of DPBS over the course of 20-30 seconds. In some embodiments, the waste reservoir is closed following the rinse step. In some embodiments, following closure of the waste reservoir, the vacuum draws out the remaining buffer from the buffer reservoir, filling the narrow channel and thereby dissolving the chemoattractive pellet at the far side of the cassette channel. In some embodiments, the vacuum is deactivated and a picture acquisition phase is initiated. In one embodiment, the picture acquisition captures one frame every 10 seconds for a duration for 30 minutes, totaling in 180 frames, though these exact parameters can and should be modified depending on experiment type and sample cell type. Thus, in some embodiments, the picture acquisition captures one frame every 1, 2, 3, 4, 5, 6, 7, 8, 9, 10, 15, 20, 30, 40, 50, or 60 seconds or 1, 2, 3, 4, 5, 6, 7, 8, 9, or 10 minutes, or a time within any two of the aforementioned times. In some embodiments, the picture acquisition captures the frames for a duration of 1, 2, 3, 4, 5, 10, 15, 20, 25, 30, 35, 40, 45, 50, 55, or 60 minutes or 1, 2, 3, 4, 5, 6, 7, 8, 9, 10, 12, 14, 16, 18, 20, 22, or 24 hours, or for a duration within any two of the aforementioned values.

In some embodiments, each of the steps described above are intended to occur in order and in correct timing without human intervention. In some embodiments, any single step may be eliminated, repeated, modified, or re-ordered depending on the nature of the experiment. In some embodiments, user intervention may be included in any given step. In some embodiments, upon assay start, the analyzer will continue with each of the phases described unless manually stopped by a user.

In some embodiments, as each frame of the cell assay is captured, it is sent via secure Ethernet connection to a remote server. In some embodiments, the remote server compiles the frames to create a time course video. In some embodiments, the remote server continuously analyzes the video as each frame is sent so as to reduce the overall time of each assay. In some embodiments, once the full assay and resulting analysis is completed, an electronic report is sent to the corresponding clients. In some embodiments, the client may include research institutes, pharmaceutical researchers, or primary care physicians. In some embodiments, analyzers are equipped with small hard drives, which store all images from the most recent assay until a new one is run. In some embodiments, the storage is provided in case connection to the data server is lost at any point during the assay due to power outage, internet connectivity issues, or other unforeseen circumstances. In some embodiments, should the analyzer lose contact with the corresponding server, all images stored on the analyzer hard drive will be resent once connection is reestablished.

In some embodiments, the analyzer described above can be designed to either have fixed or modular values for qualities including, but not limited to, field of view, focus, and photo exposure, depending on the needs of a given researcher, clinic, or project. In some embodiments, such as in a clinical setting, fixed values are highly recommended in order to ensure greatest possible consistency and accuracy, as well as the minimization of human error.

Composition and Application of Immune-Relevant Molecules

In some embodiments, the lyophilized pellet containing chemoattractant specifically contains N-Formyl-methionyl-leucyl-phenylalanine (fMLF). In some embodiments, the amount of chemoattractant includes an amount that allows for a final concentration of $10^{-8}$ M upon full gradient equilibration. In some embodiments, chemokines that may be used instead of or in addition to fMLF in order to induce relevant cell behavior include fMet, IL-8, Leukotriene B4 (LTB4), CXCL1, CXCL2, CXCL8, CXCL9, CXCL10, CXCL12, CCL2, CCL3, CCL5, CCL11, CCL19, CCL21, CX3CL1, C5a, C5b, G-CSF, GM-CSF and any combination thereof (Feng D, Nagy J A, et al. "Neutrophils Emigrate from Venules by a Transendothelial Cell Pathway in Response to FMLP." Journal of Experimental Medicine 187(6): 903-915. 1998; Gerard N P and Gerard C. "The chemotactic receptor for human C5a anaphylatoxin." Nature 349: 614-617. 1991; Kilgore K S, Flory C M, et al. "The membrane attack complex of complement induces interleukin-8 and monocyte chemoattractant protein-1 secretion from human umbilical vein endothelial cells." American Journal of Pathology 149(3): 953-961. 1996; Luster A D, Alon R, and von Andrian U H. "Immune cell migration in inflammation: present and future therapeutic targets." Nature Immunology 6: 1182-1190. 2005; Murphy P M. "The Molecular Biology of Leukocyte Chemoattractant Receptors." Annual Review of Immumology 12: 593-633. 1994; Oppenheim J J and Yang D. "Alarmins: chemotactic activators of immune response." Current Opinion in Immunology 17: 359-365. 2005; Reichel C A, Rehberg M, et al. "Ccl2 and Cc13 mediate neutrophil recruitment via induction of protein synthesis and generation of lipid mediators." Arteriosclerosis, Thrombosis, and Vascular Biology 29(11): 1787-93. 2009; Ley K. "Arrest Chemokines." Frontiers in Immunology. Editorial. 2014; Wang J M, Chen Z G, et al. "Chemotactic activity of recombinant human granulocyte colony-stimulating factor." Blood 72: 1456-1460. 1988; Wang J M, Allavena C P, and Mantovani A. "Chemotactic activity of human recombinant granulocyte-macrophage colony-stimulating factor." Immunology 60: 439-444. 1987; each of which is incorporated by reference herein in its entirety). Optimal chemoattractant compositions will vary widely depending on both the cell types of interest and the specific kind of cellular response to be investigated. In some embodiments, cellular response may be induced via doping with one or more pro-inflammatory cytokines, including IL-1, IL-3, IL-4 IL-5, IL-6, IL-7, IL-11 IL-17, IL-21, IL-1β, TNFα, stem cell factor (SCF), thrombin, erythropoietin (EPO), IFN-α, IFN-β, IFN-γ, or any other molecules implicated in relevant biological pathways (Wang J M, Allavena C P, and Mantovani A. "Chemotactic activity of human recombinant granulocyte-macrophage colony-stimulating factor." Immunology 60: 439-444. 1987; Croce M, Rigo, V, and Ferrini S. "IL-21: a pleiotropic cytokine with potential applications in oncology." Journal of Immunology Research 2015: 1-15. 2015; Klinger M H F and Jelkmann W. "Role of Blood Platelets in Infection and Inflammation." Journal of Interferon & Cytokine Research 22: 913-922. 2002; each of which is incorporated by reference herein in its entirety). In some embodiments, the use of one or more of these inflammation-mediating molecules in the context of the investigative platform described herein may prove particularly useful for the purposes of exploring specific pathways for therapeutic application or for simulating inflammatory response in healthy samples.

In some embodiments, adhesion molecules are additionally used to functionalize the surface of the chemotaxis cassette to facilitate a desired cellular behavior. In some embodiments, the granulocyte-oriented iteration of the platform utilizes one or more of P-selectin, fibronectin, or collagen I to facilitate cell arrest and crawling motility. In some embodiments, several other adhesion-mediating molecules may be used instead of or in addition to one or more of P-selectin, fibronectin, or collagen I, including collagen II, collagen III, collagen IV, fibrogen, fibrinogen, vinculin, laminin, gelatin, VCAM-1, ICAM-1, INCAM-110, VLA-4, CD2, LFA-1, LFA-3, von Willebrand's factor (VWF), vitronectin, thrombospondin (TSP), E-selectin, and L-selectin (Albelda S M and Buck C A. "Integrins and other cell adhesion molecules." The FASEB Journal 4(11): 2868-2880. 1990; Gumbiner B M. "Cell Adhesion: The Molecular Basis of Tissue Architecture and Morphogenesis." Cell 84: 345-357. 1996; McEver R P and Cummings R D. "Role of PSGL-1 Binding to Selectins in Leukocyte Recruitment." Journal of Clinical Investigation 100(3): 485-492. 1997; Vestweber D and Blanks J E. "Mechanisms that regulate the function of the selectins and their ligands." Physiological Reviews 79(1): 181-213. 1999; each of which is incorporated by reference herein in its entirety).

Induction of Immune Cell Response

In some embodiments, approximately 10 μL of whole blood is deposited into the chemotaxis cassette through a sample injection location on the cassette that is sealed following sample introduction to allow for vacuum mediated rinsing. In some embodiments, the amount of sample is in the range of about 1 to 20 μL. In some embodiments, upon sample introduction, the cassette is placed into the corresponding analyzer. In some embodiments, the initial blood sample is diluted at a rate of approximately 4 parts DPBS to 1 part blood and a stationary incubation period of approximately 5 minutes elapses to allow for sufficient cell adhesion to the cassette surface. In some embodiments, following this incubation period, a series of gentle rinses are used to remove non-adherent cells and other debris from the field of view. In some embodiments, the interior walls of the chemotaxis cassette are coated with heparin. In some embodiments, heparin serves to prevent the coagulation of red blood cells, thereby allowing for easier clearance of the red blood cells. In some embodiments, after rinsing, the waste reservoir of the cassette is closed and a fill step occurs wherein buffer fills the entire channel. In some embodiments, the buffer is DPBS. In some embodiments, the amount of buffer is in the range from 0.1 to 2 mL. In some embodiments, the amount of buffer is 1 mL. In some embodiments, the buffer dissolves the pellet containing chemoattractive chemicals. In some embodiments, the buffer creates a chemo-gradient, thereby instigating immune response in captured cells.

Data Collection and Analysis

In some embodiments, upon the initiation of desired cell response, a program is run on the analyzer to capture dynamic biophysical cell behavior utilizing on-board optical equipment. In some embodiments, the optical equipment includes one or more of a phase-contrast at 400× total magnification, a camera attachment, or an Ethernet connectivity to a remote server). In one embodiment, one picture is captured every 10 seconds for a duration of 30 minutes, resulting in a time-lapse video of cellular movement with a total of 180 frames. All of these parameters can be modified to optimally fit research systems. For example, in some embodiments, one picture is captured every 1, 2, 3, 4, 5, 6, 7, 8, 9, 10, 15, 20, 30, 40, 50, or 60 seconds or 1, 2, 3, 4, 5, 6, 7, 8, 9, or 10 minutes, or a time within any two of the aforementioned times. In some embodiments, the pictures are captured for a duration of 1, 2, 3, 4, 5, 10, 15, 20, 25, 30, 35, 40, 45, 50, 55, or 60 minutes or 1, 2, 3, 4, 5, 6, 7, 8, 9, 10, 12, 14, 16, 18, 20, 22, or 24 hours, or for a duration within any two of the aforementioned values. In some embodiments, following acquisition, these frames are sent electronically to an offsite server to conduct computational analysis.

Figure 3A:
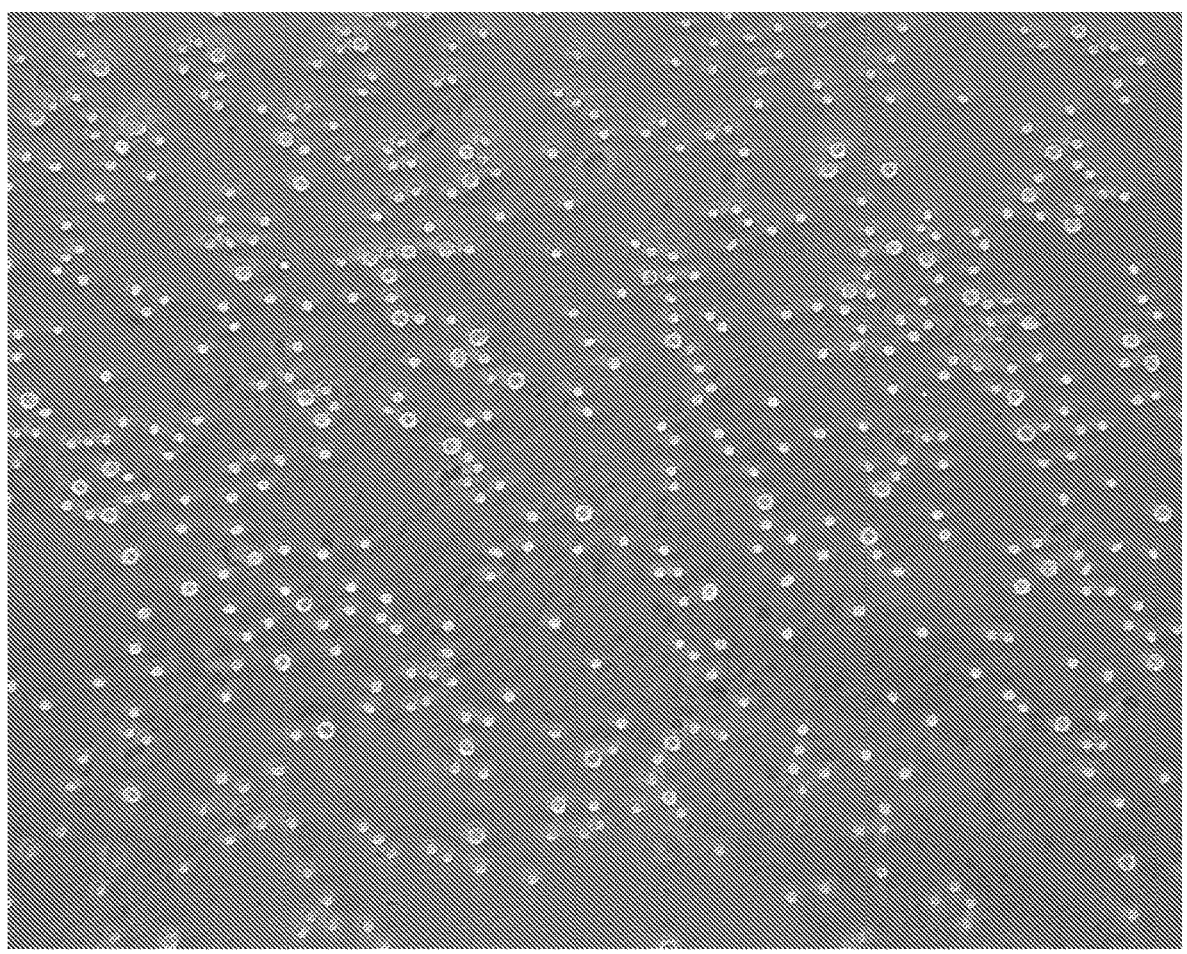
FIGS. 3A and 3B depict still-frame images generated by the cell tracking image processing system.
Figure 3B:
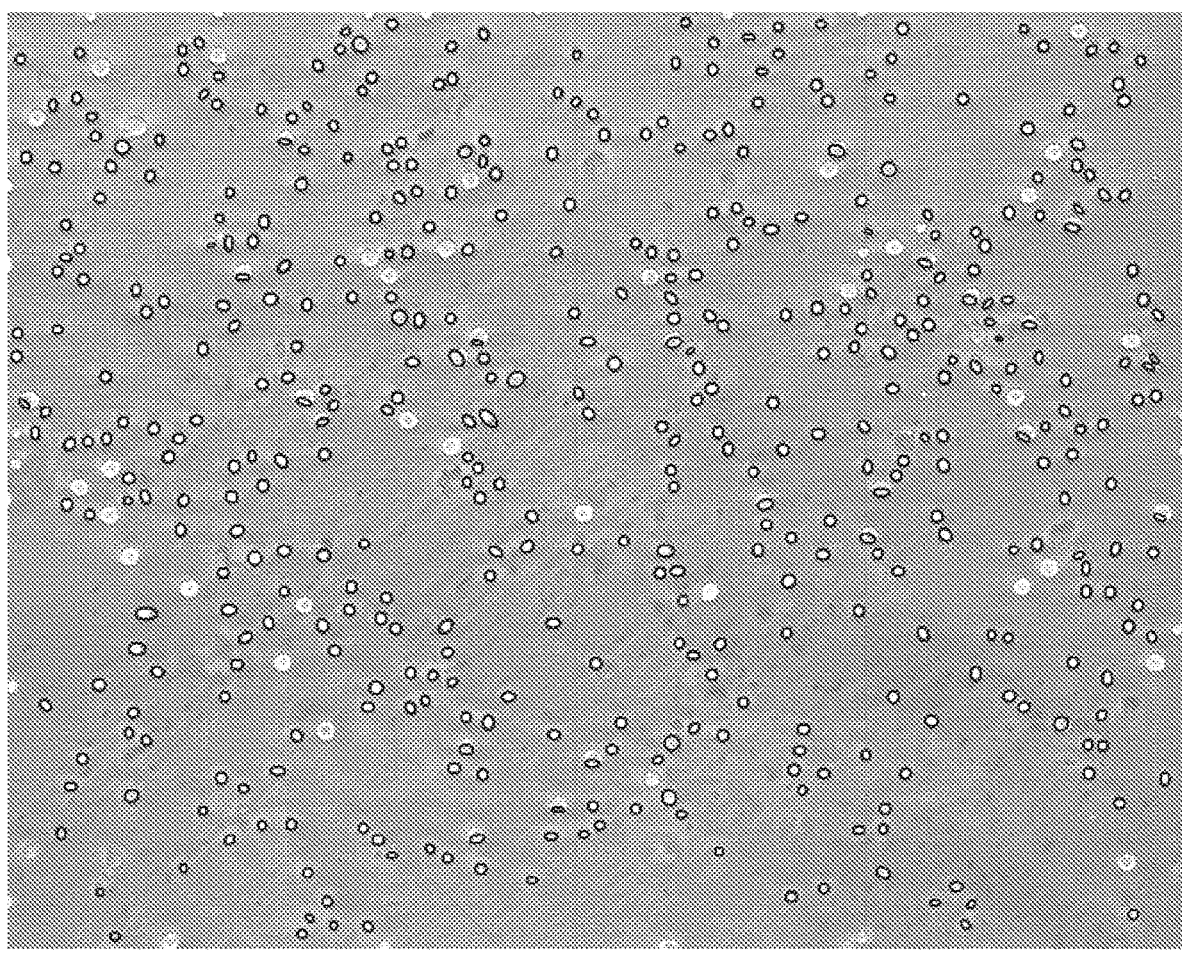

FIGS. 3A and 3B depict still-frame images generated by the cell tracking image processing system. FIG. 3A depicts a raw still-frame image. FIG. 3B depicts a still-frame image outlining cells that are tracked and measured. Cells having a halo (red blood cells) are not tracked and measured. Similarly, other cells that have the wrong geometry or do not exhibit typical immune cell behavior due to inactivity or that are non-living are also not tracked and measured.

In some embodiments, the image processing system employed by the platform utilizes advanced computer vision techniques, as described in detailed below. In some embodiments, the advanced computer vision techniques collect and measure a one or more biophysical variables of each cell in a given assay. In some embodiments, the one or more biophysical variables of each cell includes cell morphology, cell position, cell directionality, cell orientation, cell perimeter, cell luminance, cell area, cell velocity, cell speed, cell acceleration, cell direction, cell circularity, cellular branching events, cell branch length, cell image moments (or Hu moments), cell eccentricity, cell path trends, cell spreading, cell grouping, neutrophil extracellular trap (NET) formations, degranulation events, or overall prevalence. In some embodiments, the rates of change for all of the aforementioned variables are also measured. In some embodiments, the one or more biophysical variables are collected at a single-cell level. In some embodiments, the one or more biophysical variables are averaged to assay population levels in order to properly assess the inflammation exhibited in a sampled patient. In some embodiments, the one or more biophysical variables are automatically measured by an image processing system. In some embodiments, a final inflammation metric is produced by means of combining each measured variable, weighting in proportion of variable relevance as discerned by machine learning software.

As used herein, the term "machine learning" is a branch of artificial intelligence in the field of computer science that involves the construction of systems capable of changing their algorithmic behavior in response to dynamic input data. In essence, programs that utilize machine learning can continuously take in new information and actively respond to that information, effectively learning and adapting in a responsive manner. In some embodiments, a machine learning system is provided for use in connection with the methods provided herein in order to learn the key differences in systemic inflammation present across documented severities and associated diseases. In some embodiments, the machine learning system functions by collecting various data sets from each assay run, stored and cataloged on a remote server, and comparing those data sets to one another in order to categorize them into inflammatory subsets based on behavioral similarity. In some embodiments, an algorithm is generated to take the measurements for each new assay and cross-reference them with a pre-existing databank of known conditions to accurately quantify present inflammation. In some embodiments, the system runs without the need for human input or intervention.

In some embodiments, the algorithms generated and used in this diagnostic strategy continue to improve with each new documented assay, making for a more robust and sensitive interpretation of results as patient number increases. In some embodiments, methods of data collection and interpretation allow for disease-specific identification based not only on the perceived severity of inflammation present in a sample, but also on the signature behaviors exhibited by individual cells. In some embodiments, the data acquired over the course of the assay's lifespan will yield highly significant implications regarding the nature of immune response in many diseases and disease super-types. In some embodiments, streamlined identification of new therapeutics may be generated as a result of the machine learning system.

Assay Uses and Applications

Using the methods described herein, some embodiments provide for a system to quantitatively assess levels of systemic immune cell activity present in a given blood sample.

Figure 4:
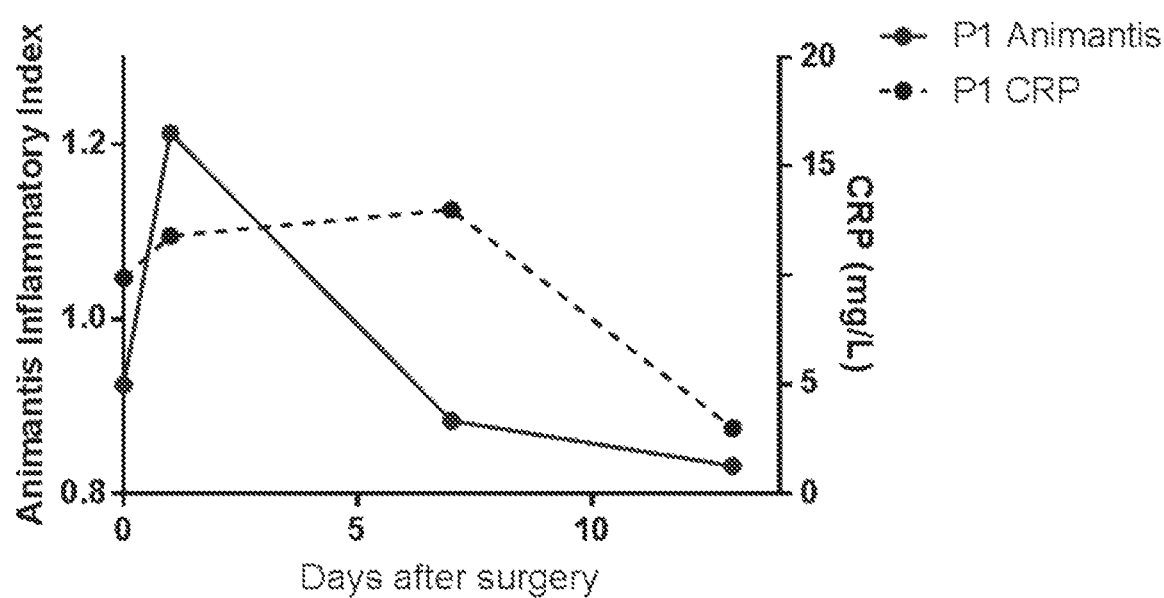
FIG. 4 depicts inflammation data from patients over the course of surgery and recovery.

FIG. 4 depicts inflammation data from patients over the course of surgery and recovery.

Figure 5:
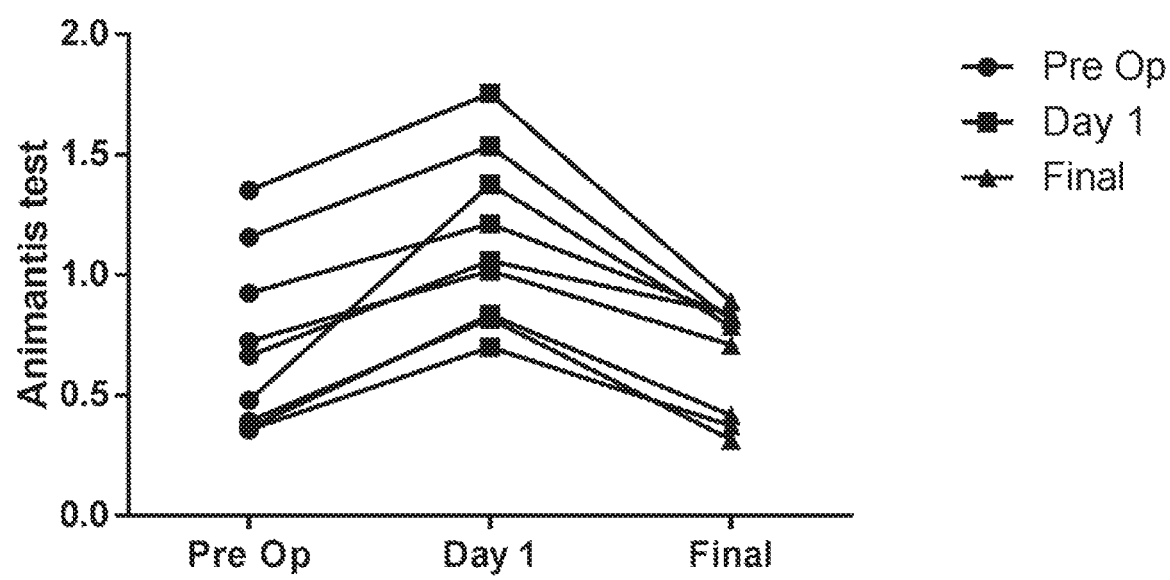
FIG. 5 depicts the calculated inflammation trends of all patients from the data of FIG. 4 prior to operation, at day 1, and at a final measurement.

FIG. 5 depicts the calculated inflammation trends of all patients from the data of FIG. 4 prior to operation, at day 1, and at a final measurement.

Figure 6:
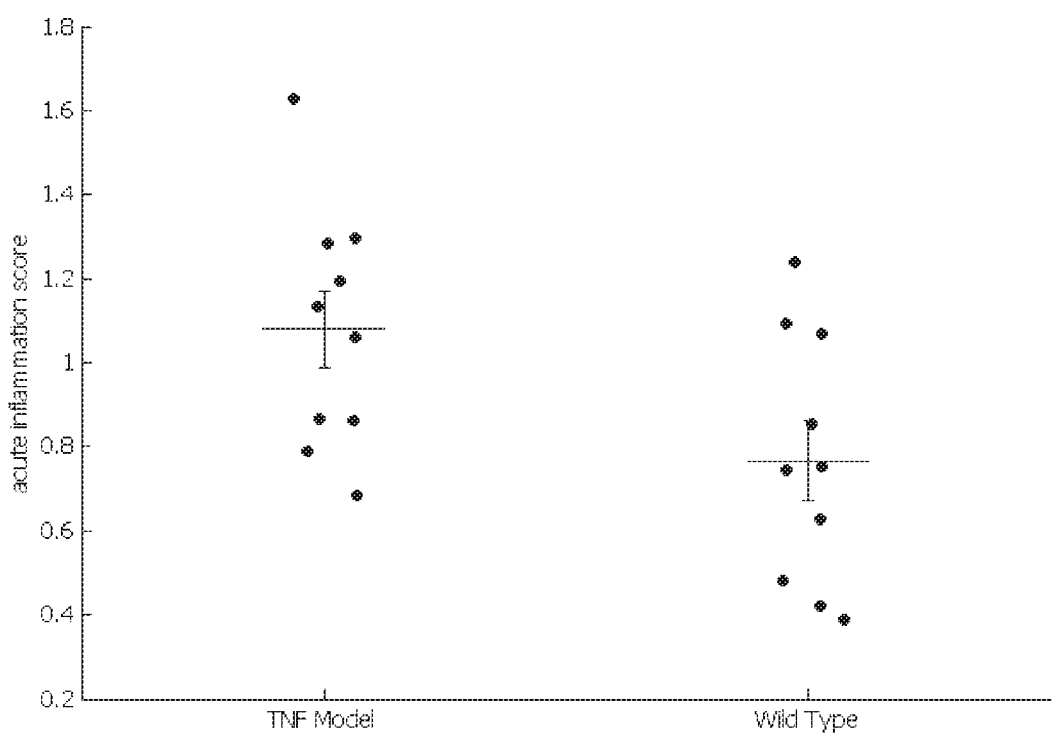
FIG. 6 is a graphical representation of inflammation scores for mice derived using an embodiment of the immune analysis provided herein.

FIG. 6 is a graphical representation of inflammation scores for mice derived using an embodiment of the immune analysis provided herein. TNF-α mice, often used as an animal model for inflammatory bowel disease and arthritis, demonstrated a marked increase in present inflammation relative to wild-type counterparts.

Figure 7:
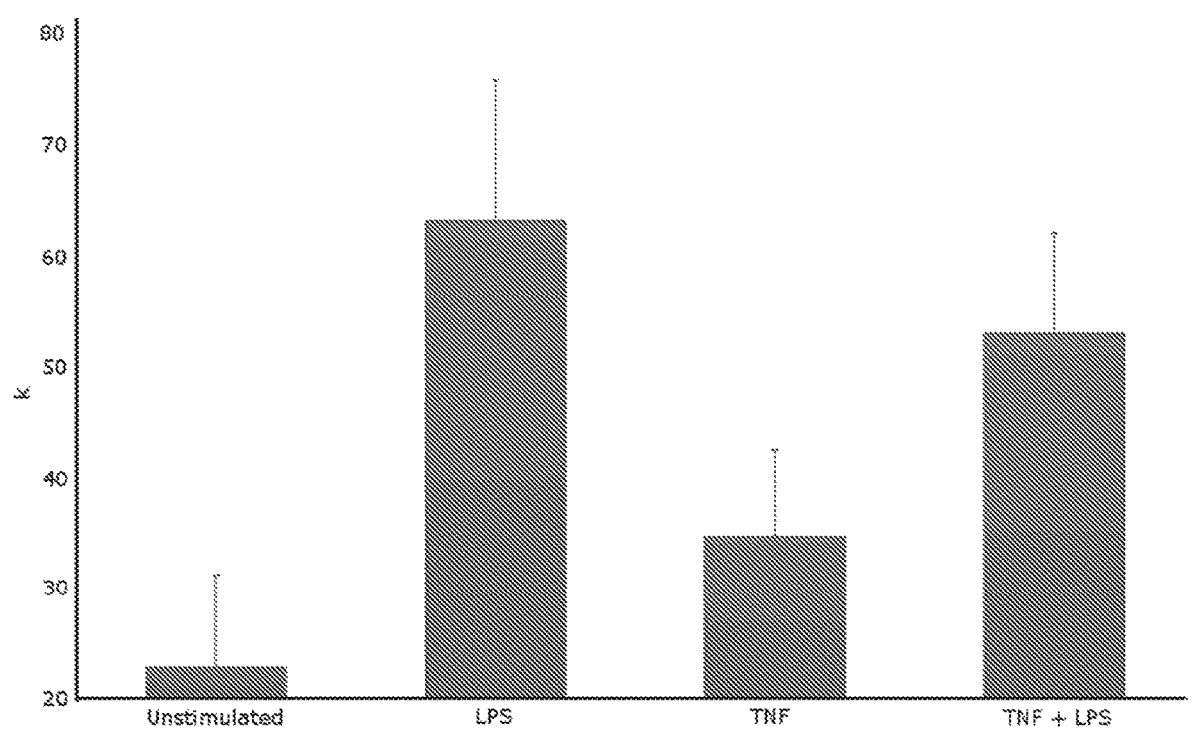
FIG. 7 is a graphical representation of the directional displacement of cell population sets as measured using an embodiment of the immune platform described herein.

FIG. 7 is a graphical representation of the directional displacement of cell population sets as measured using an embodiment of the immune platform described herein. The four conditions, unstimulated, lipopolysaccharide (LPS), tumor necrosis factor (TNF), and TNF+LPS indicate that directional displacement is greatly affected by the presence of bacterial byproducts (such as LPS), whereas it is minimally affected by the presence of TNF (an autologous immune response). These results suggest that in some embodiments, the immune platform is suitable for diagnostic cases of bacteria-mediated sepsis.

In some embodiments, including in a clinical setting, the platform described herein may be used as a diagnostic tool, allowing physicians to make informed treatment decisions for complicated diseases based on symptoms that are currently gauged only by surveys, patient testimony, and other insufficient markers. Even independent of cross-patient inflammation scores facilitated by data grouping, in some embodiments of the platform described herein is provided a fast, reliable, and cost-effective means of tracking an individual patient's progress over the course of treatment and disease progression. Particularly with inflammation-mediated diseases, high degrees of patient variability make it difficult to predict treatment efficacy in advance, and as a result patients often endure ineffective treatment regimens for months or even years. Using the platform as described in some embodiments herein to assess patient inflammation in a short timescale, therapies may be deemed effective or ineffective much earlier in the treatment process, thereby significantly reducing patient suffering and unnecessary cost.

In some embodiments, the assays provided herein are used to inform proper dosing and prescribing of immune-modulatory regimens on a case-by-case basis, such as anti-inflammatories and immunotherapy. Currently, patients who suffer from inflammation-mediated diseases, such as lupus, asthma, COPD, psoriasis, sepsis, inflammatory bowel disease, or rheumatoid arthritis, are most often treated with standard-dosage immunosuppressant drugs, although it is known that different patients do not always respond similarly to the same therapeutic regimen. Using the platform according to some embodiments provided herein to gauge immune cell response to variable drug dosing and prescribing in vitro, it is possible to predict the potential effectiveness of a given regimen before beginning treatment, preventing unnecessary cost and improving overall patient care. In some embodiments of the methodology described herein is provided an investigation and treatment guidance of several other disease types, including many types of cancer and neurodegenerative diseases, specifically Alzheimer's disease, multiple sclerosis, and Parkinson's disease (Balk S H, Cha M Y, et al. "Migration of neutrophils targeting amyloid plaques in Alzheimer's disease mouse model." *Neurobiology Aging* 35(6): 1286-1292. 2014; Capsoni F, Ongari A M, et al. "Effect of Efalizumab on neutrophil and monocyte functions in patients with psoriasis." *International Journal of Immunopathology and Pharmacology* 21(2): 437-45. 2008; Carter L and Wallace J L. "Alterations in rat peripheral blood neutrophil function as a consequence of colitis." *Digestive Diseases and Sciences* 40(1): 192-7. 1995; Clark R A, Kimball H R, and Decker J L. "Neutrophil chemotaxis in systemic lupus erythematosus." *Annals of the Rheumatic Diseases* 33: 167-72. 1974; Corhay J L, Moermans C, et al. "Increased of exhaled breath condensate neutrophil chemotaxis in acute exacerbation of COPD." *Respiratory Research* 15(115): 1-11. 2014; Demaret J, Venet F, et al. "Marked alterations of neutrophil functions during sepsis-induced immunosuppression." *Journal of Leukocyte Biology* 98(6): 1081-90. 2015; Eruslanov E B, Bhojnagarwala P S, et al. "Tumor-associated neutrophils stimulate T cell responses in early-stage human lung cancer." *Journal of Clinical Investigation* 124(12): 5466-80. 2014; Fournier B M and Parkos C A. "The role of neutrophils during intestinal inflammation." *Nature Review* 5(4): 354-66. 2012; Horvath S and Ritz B R. "Increased epigenetic age and granulocyte counts in the blood of Parkinson's disease patients." *Aging* 7(12): 1-13. 2015; Kaplan M J. "Neutrophils in the pathogenesis and manifestations of SLE." *National Review of Rheumatology* 7(12): 691-99. 2011; Lavinskiene S, Bajoriuiene I, et al. "Sputum neutrophil counts after bronchial allergen challenge is related to peripheral blood neutrophil chemotaxis in asthma patients." *Inflammation Research* 63: 951-9. 2014; Lu H, Kuang Y H, et al. "CD147 is highly expressed on peripheral blood neutrophils from patients with psoriasis and induces neutrophil chemotaxis." *Journal of Dermatology* 37(12): 1053-6. 2010; Mantovani A. "Macrophages, Neutrophils and Cancer: A Double Edged Sword." *New Journal of Science* Epub. 2014; Mitter N M, Wang J, et al. "Anti-inflammatory mechanisms of IFN-γ studied in experimental autoimmune encephalomyelitis reveal neutrophils as a potential target in multiple sclerosis." *Frontiers in Neuroscience* 1-13. 2015; Mosca T, Menezes M C, et al. "Chemotactic and Phagocytic Activity of Blood Neutrophils in Allergic Asthma." *Immunological Investigations* 44(5): 509-20. 2015; Paschke S, Weidner A F, et al. "Inhibition of neutrophil chemotaxis by colchicine is modulated through viscoelastic properties of subcellular compartments." *Journal of Leukocyte Biology* 94: 1091-96. 2012; Rudolph V, Steven D, et al. "Coronary plaque injury triggers neutrophil activation in patients with coronary artery disease." *Free Radical Biology & Medicine* 42: 460-5. 2007; Rumble J M, Huber A K, et al. "Neutrophil-related factors as biomarkers in EAE and MS." *The Journal of Experimental Medicine* 212(1): 23-35. 2015; Simmons S B, Liggitt D, and Goverman J M. "Cytokine-regulated neutrophil recruitment is required for brain but not spinal cord inflammation during EAE." *Journal of Immunology* 193(2): 555-563. 2014; Trung P H, Prieur A M, and Griscelli C. "Neutrophil chemotaxis in juvenile chronic arthritis." *Annals of the Rheumatic Diseases* 39: 481-84. 1980; Uzel G, Kleiner D E, et al. "Dysfunctional LAD-1 neutrophils and colitis." *Gastroenterology* 121(4): 958-64. 2001; Wagner J G and Roth R A. "Neutrophil migration during endotoxemia." *Journal of Leukocyte Biology* 66: 10-24. 1999; Wu J, Hillier C, et al. "A Microfluidic Platform for Evaluating Neutrophil Chemotaxis Induced by Sputum from COPD Patients." *PLoS One* 10(5):1-13. 2015; Yan J, Kloecker G, et al. "Human polymorphonuclear neutrophils specifically recognize and kill cancerous cells." *OncoImmunology* 3(7): Epub. 2014; Zhu X, Xiao L, et al. "Cyr61 is involved in neutrophil infiltration in joints by inducing IL-8 production by fibroblast-like synoviocytes in rheumatoid arthritis." *Arthritis Research & Therapy* 15(6): 187. 2013; Zonneveld R, Molema G, and Plotz F B. "Analyzing Neutrophil Morphology, Mechanics, and Motility in Sepsis: Options and Challenges for Novel Bedside Technologies." *Critical Care Medicine* Epub. 2015; the disclosure of each of which is incorporated herein in reference in its entirety).

In some embodiments, provided herein are assays, methods, and systems for assessing, analyzing, or studying an immune response of a subject. In some embodiments, the subject suffers from or is suspected of suffering from one or more of cancer, atherosclerosis, sepsis, asthma, inflammatory bowel disease, chronic obstructive pulmonary disease, allergies, systemic lupus erythematosus, lupus nephritis, vasculitis, osteoarthritis, psoriatic arthritis, rheumatoid arthritis, ankylosing spondylitis, psoriasis, non-alcoholic fatty liver disease, cirrhosis, type I diabetes, type II diabetes, diabetes mellitus, multiple sclerosis, Alzheimer's disease, Parkinson's disease, cystic fibrosis, eosinophilic esophagitis, acute myocardial infarction, pneumonia, heart failure, hospital readmission following surgical procedure, idiopathic pulmonary fibrosis, organ transplant rejection and/or hospital readmission, implanted medical device rejection, or general immune system assessment.

As used herein, the term "cancer" refers to cellular tumor. Cancer cells having the capacity for autonomous growth, such as an abnormal state or a condition characterized by rapidly proliferating cell growth. The term is meant to include all types of cancerous growths or oncogenic processes, metastatic tissues or malignantly transformed cells, tissues, or organs, irrespective of histopathologic type, or stage of invasiveness. Examples of cancers include, but are not limited to, carcinoma and sarcoma such as leukemia, sarcomas, osteosarcoma, lymphomas, melanoma, ovarian cancer, skin cancer, testicular cancer, gastric cancer, pancreatic cancer, renal cancer, breast cancer, prostate colorectal cancer, cancer of head and neck, brain cancer, esophageal cancer, bladder cancer, adrenal cortical cancer, lung cancer, bronchus cancer, endometrial cancer, nasopharyngeal cancer, cervical or hepatic cancer, or cancer of unknown primary site.

As used herein, the term "chronic obstructive pulmonary disease (COPD)" refers to a chronic progressive lung disease. COPD can include, for example, chronic bronchitis and emphysema.

As used herein, the term 'inflammatory bowel disease" refers to a group of diseases of inflammatory conditions of the colon or small intestine. In some embodiments, inflammatory bowel disease includes diseases that cause inflammation of the intestines, such as Crohn's disease, ulcerative colitis, necrotizing enterocolitis, severe acute gastroenteritis, chronic gastroenteritis, cholera, as well as other chronic infections of the bowel.

As used herein, the term "allergies" refers to diseases and conditions wherein a patient demonstrates a hypersensitive or allergic reaction to one or more substances or stimuli such as drugs, food stuffs, plants, animals, plant material, etc. and as a result has an increased immune response. Such immune responses can include anaphylaxis, allergic rhinitis, asthma, skin sensitivity such as urticaria, eczema, and allergic contact dermatitis and ocular allergies such as allergic conjunctivitis and contact allergy.

As used herein, the term "heart failure" refers to an abnormality of cardiac function where the heart does not pump blood at the rate needed for the requirements of metabolizing tissues. Heart failure includes a wide range of disease states such as congestive heart failure, myocardial infarction, tachyarrhythmia, familial hypertrophic cardiomyopathy, ischemic heart disease, idiopathic dilated cardiomyopathy, myocarditis and the like. The heart failure can be caused by any number of factors, including, without limitation, ischemic, congenital, rheumatic, viral, toxic or idiopathic forms. Chronic cardiac hypertrophy is a significantly diseased state which is a precursor to congestive heart failure and cardiac arrest.

In some embodiments, the assays provided herein are also suitable for disease-specific diagnostics, especially wherein robust machine learning has taken place. Different inflammation-mediated diseases often result in similar symptomatic phenotypes, making them notoriously difficult to differentiate and diagnosis until significant tissue damage has already occurred. By looking at immunological systems at the cellular level, it is possible to identify biophysical cell characteristics signature to specific disease types, allowing for differential diagnosis at an earlier stage in the treatment process.

The novel technology detailed in some embodiments herein has implications beyond the clinical setting as well, lending itself to utilization in the worlds of academic research and pharmaceutical development. In some embodiments, the platform fits well into the workflow of several stages of basic research and the drug development process, either as a complementary metric to contextualize other collected data or as an independent marker capable of representing complex molecular processes in a distilled format. For example, because this assay is able to reliably and objectively classify patients by immune profile, it may prove suitable for patient staging in clinical trials, identifying in advance patients who may be more likely to respond to a specific treatment. Such an application would potentially improve clinical results for new therapeutics and contribute to the increasingly growing demand for personalized approaches to medicine. Additionally, the assay could be used in earlier stages of therapeutic development, up to and including drug discovery. While this platform has been designed principally designed for use with primary human samples, the concepts and methodologies detailed here could just as well be applied to other mammalian immune cells, specifically those of mice and rats, with minimal or no modulation. This would enable discovery-phase researchers to rapidly assess the resulting immune response to high-throughput drug screening with a simple and holistic measure, drastically reducing cost while increasing rates of project completion.

Description of Image Processing System

Overview

The input to the image processing system is a video of living immune cells taken from a patient blood sample. The returned value represents an inflammatory index calculated using computer vision, object tracking, and machine learning techniques, though more nuanced or less-processed data can be returned for specific implementations.

Figure 8:
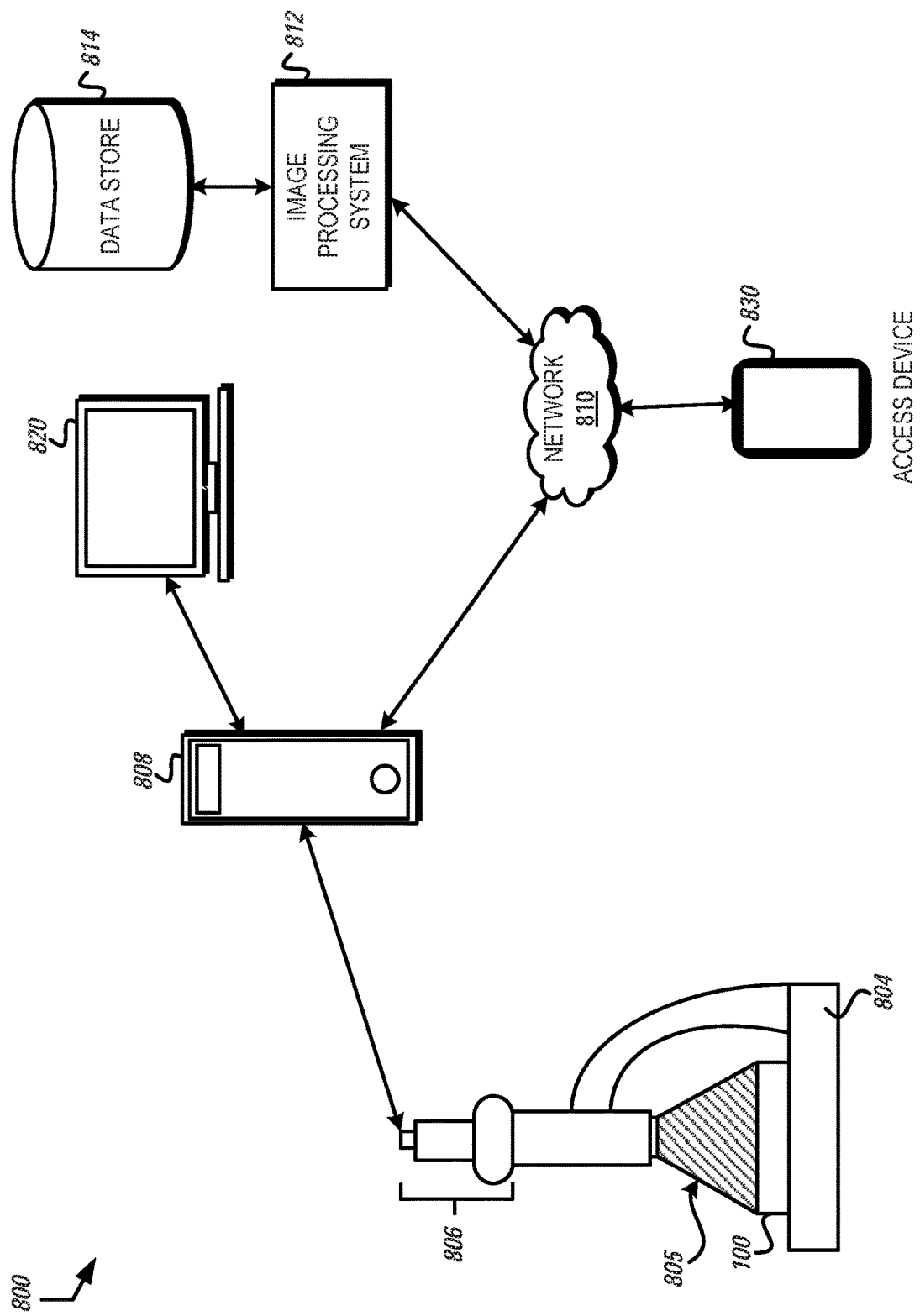
FIG. 8 is a pictorial diagram showing an illustrative image processing system environment.

FIG. 8 is a pictorial diagram showing an illustrative image processing system environment. The environment 800 includes a microscope 804. The microscope 804 may include or be fitted with an imaging device 806. The imaging device 806 may be a camera configured to capture magnified images of the chemotaxis cassette 100. A field of view 805 of the microscope 804 may be focused to capture the chemotaxis cassette 100. The focusing of the microscope 804 and/or imaging device 806 may be performed manually or via a control server 808. The control server 808 may provide configuration commands to adjust an operational characteristic of the microscope 804 and/or imaging device 806. For example, the frame rate, color levels, or resolution may be adjusted for a given assay. In some implementations the adjustment may be based on an identification of the assay. Using assay identification information, a desired configuration may be obtained such as from a memory accessible by the control server 808.

A display 820 may be coupled with the control server 808. In some implementations, the display 820 may present one or more user interfaces to: receive input information regarding an assay and/or configuration of the microscope 804 and/or imaging device 806, show one or more images captured by the imaging device 806, present one or more results of an assay.

As image data is received by the control server 808, the image data may be transmitted via a network 810 to an image processing system 812 for analysis as will be described below. The image data may be analyzed in real time (e.g., as received) or stored in a data store 814 for analysis at a later time. The network 810 may include one or more of a LAN, WAN, cellular network, satellite network, and/or the Internet. Connection to the network 810 may be, for example, via a wired, wireless, or combination of wired and wireless, communication link. The communications via the network 810 may include messages. The messages may be formatted and transmitted according to a standardized protocol such as TCP/IP, HTTP, FTP, or the like.

In some implementations, an access device 830 may be included in the environment 800 to allow review of the image data and results generated by the image processing system. The access device 830 may present one or more user interfaces to receive inputs that can be used to capture and/or analyze image data. The access device 830 may be a portable electronic communication device such as a smartphone or a tablet computer. The access device 830 may be a desktop computer or server.

Image Processing System Description

Example features that may be included in an image processing system are shown in pseudocode in LISTING 1.

LISTING 1

```
Main(videoFrames)
    standardizedFrames ← Standardize(videoFrames)
    cellBlobs ←•Ø
    i ← 0
    for frame in standardizedFrames do
        cellBlobs(i) ← DetectCells(frame)
        i ← i + 1
    end
    allCells ← TrackCells(cellBlobs)
    featureVector ← CalculateMetrics(allCells)
    inflammatoryIndex ← Classify(featureVector)
    return inflammatoryIndex
```

The input to the main function includes a set of images that are the frames from a video of moving immune cells taken from a patient blood sample. In the following subsections, the helper functions called out in LISTING 1 (Standardize, DetectCells, TrackCells, CalculateMetrics, and Classify) are explained individually. The helper functions may be implemented as software or hardware. When implemented as software, the functions may be implemented as specific instructions executable by one or more processors included in a computing device that cause the computing device to perform the features described. When implemented as hardware, the functions may be implemented using specific circuitry configured to receive the identified input signals and provide the specified output signals.

Standardize(videoFrames)
 a. Input: A set of image-frames from a sample video
 b. Output: A set of standardized frames
 c. Description: Because later calculations may require comparisons between frames in the video, the frames may be standardized so that they have comparable means and variances in pixel values. To do this, each frame's pixel values may be shifted so that they have one or more common aspects such as mean and standard deviation. LISTING 2 provides one example pseudocode expression of standardization.

LISTING 2

```
Standardize(videoFrames)
    meanAccumulator ←•Ø
        stDevAccumulator ←•Ø
    i ← 0
    for frame in videoFrames do
        meanAccumulator(i) ← Mean(frame)
        stDevAccumulator(i) ← StDev(frame)
        i ← i + 1
    end
    meanOfMeans ← Mean(meanAccumulator)
    meanOfStDevs ← Mean(stDevAccumulator)
    standardizedFrames ←•Ø
    for frame in videoFrames do
        stDevCorrection ← meanOfStDevs / StDev(frame)
        standardizedFrames(i) ← ((frame − Mean(frame))...
            * stDevCorrection) + meanOfMeans
    end
    return standardizedFrames
```

The values chosen for the standardized mean and standard deviation may be the average values of these two metrics across all frames or a portion of the frames. The portion of the frames may be dynamically determined based on a value detected by the device performing the standardization. For example, the device may detect a format used to encode the frames and select the portion of the frames for analysis based on the format. As another example, the device may detect resources available to the device such as processing resources, power resources, memory resources, bandwidth or the like. Based on the available resources, fewer or additional frames may be used to ensure the resource demands placed on the device for standardizing the frames do not exceed the available resources.

DetectCells(standardizedFrames)
 a. Input: A set of standardized video frames
 b. Output: A set of blobs representing probable cell pixels
 c. Description: Likely cell locations may be determined based on a combination of the temporal variance in pixel values (i.e. moving objects between frames, such as in the work by Brandes et al. (Brandes S, et al. "Automated segmentation and tracking of non-rigid objects in time-lapse microscopy videos of polymorphonuclear neutrophils." Medical Image Analysis 20(1): 34-51. 2015; the disclosure of which is herein incorporated by reference in its entirety)) and pixel variance from the image mean (e.g., exceptionally bright or dark objects). These variances may be combined and/or thresholded to create a binary image of likely locations, from which blobs (connected components) may be extracted. FIG. 3B provides a graphical representation of an image including detected cells. LISTING 3 presents a pseudocode example of this process; further details appear in the section below entitled "Algorithm Descriptions."

LISTING 3

```
DetectCells(standardizedFrames)
    cellBlobs ←•Ø
    for i in 0:standardizedFrames.size( ) do
        tVariance ← GetTemporalVariance(i)
        mVariance ← GetVarianceFromMean(i)
        combinedVariance ← (θ * tVariance + 1)...
```

LISTING 3

```
        * ((1 - θ) * mVariance + 1)
        threshold ← Mean(combinedVariance)...
                    + n * StDev(combinedVariance)
        binaryImage ← combinedVariance > threshold
        cellBlobs(i) ← FindBlobs(binaryImage)
    end
    return cellBlobs
GetTemporalVariance(i)
    valueAccumulator ← Ø
    windowStart ← Max(0, i - m)
    windowEnd ← Min(standardizedFrames.size( ), i + m)
    for j in windowStart:windowEnd do
        valueAccumulator ← valueAccumulator +...
                            standardizedFrames(j)
    end
    windowMean ← valueAccumulator / (windowEnd -...
                            windowStart)
    tVariance ← (standardizedFrames(i) - windowMean)²
    return tVariance
GetVarianceFromMean(i)
    mVariance ← (standardizedFrames(i) -...
                            Mean(standardizedFrames(i)))²
    return mVariance
FindBlobs(binaryImage)
    booleanVisitedMap ← Ø
    cellBlobs ← Ø
    for pixel in binaryImage do
        if booleanVisitedMap(pixel) = false do
            if pixel = 1 do
                newBlob ← Ø
                newBlob.add(pixel)
                booleanVisitedMap(pixel) ← true
                pixelNeighbors ← pixel.neighbors( )
                for neighbor in pixelNeighbors do
                        if booleanVisitedMap(neighbor) = false and...
                                neighbor = 1 do
                            newBlob.add(neighbor)
                            booleanVisitedMap(neighbor) ← true
                            pixelNeighbors.add(neighbor.neighbors( ))
                        end
                end
                cellBlobs.add(newBlob)
            end
        else
            continue
        end
    end
    return cellBlobs
```

TrackCells(cellBlobs)

a. Input: A set of probable cell blobs b. Output: A set of cell objects, tracked across frames c. Description: The track association function can determine the most likely paths of each cell throughout the video as determined by, for example, the highest probability linking of cell blobs between frames. This can be achieved through an implementation of the joint probabilistic data association filter (JPDAF) (Bar-Shalom Y, Daum F, and Huang J. "The probabilistic data association filter." *Control Systems, IEEE* 29(6): 82-100. 2009; the disclosure of which is herein incorporated by reference in its entirety) that uses multiple particle filters to predict the updated state of each cell between frames. The cell objects constructed in this function may encode per-cell information such as the position, area, orientation, major axis length, minor axis length, and perimeter length in each frame that the cell is visible. LISTING 4 gives an example pseudocode implementation using only cell positions as the state that is being tracked.

LISTING 4

```
TrackCells(cellBlobs)
    allCells ←•Ø
    cellHypotheses ←•cellBlobs.fromFrame(0)
    for i in 1:videoFrames.size( ) do
        for cell in cellHypotheses do
            cell.particles ←•GenerateParticles(cell)
            cell.particleWeights ←•WeightParticles(cell)
        end
        cellAssignments ←•AssignCells(cellHypotheses,...
                            cellBlobs.fromFrame(i))
        for cell in cellHypotheses do
            bestDetection ←•Max(cellAssignments)
            cell.updatePosition(bestDetection)
        end
    end
    for cell in cellHypotheses do
        if cell.trackLength > minTrackLength do
        allCells.add(cell)
            end
    end
    return allCell
GenerateParticles(cell)
    particles ←•Ø
```

LISTING 4

```
        oldParticles ←•cell.particles
        for i in 1:nParticles do
                randomProbability ←•RandomDouble( )
                randomUpdateScale ←•RandomDouble( )
                randomInteger ←•RandomIntegerInRange(1, nParticles)
                if randomProbability < cell.mobileProbability do
                     newParticle ←•oldParticles(randomInteger) +...
                             randomUpdateScale * mobileMotionModel
                     particles.add(newParticle)
                else
                     newParticle ←•oldParticles(randomInteger) +...
                             randomUpdateScale * stationaryMotionModel
                     particles.add(newParticle)
                end
        end
        return particles
WeightParticles(cell)
        particleWeights ←•Ø
        for particle in cell.particles do
                meanSquaredError ←•(particle.pixels − template)² /...
                          template.size
                particleWeights.add(meanSquaredError)
        end
        return particleWeight
AssignCells(cells, blobs)
        assignProbabilities ←•Ø
        for blob in blobs do
                for cell in cells do
                    meanSquaredError ←•(cell.pixels − blob)² /...
                           cell.size
                    assignProbabilities.add(meanSquaredError)
                end
        end
        cellAssignments ←•Ø
        booleanBlobAssigned ←•Ø
        for cell in cells do
                while true
                    bestMatch ←•Min(assignProbabilities.forCell(cell))
                    if booleanBlobAssigned(bestMatch) = true
                          assignProbabilities.remove(bestMatch)
                          continue
                    else
                          break
                    end
                end
                cellAssignments ←•(cell, bestMatch)
                booleanBlobAssigned(bestMatch) ←•true
        end
        return cellAssignments
```

Note that certain particle filter implementations can account for different cell behaviors depending on their current mode of motion (e.g., mobile vs. stationary), similar to the Markov chain Monte Carlo (MCMC) approach taken by Khan et al. when accounting for interacting targets (Khan Z, Balch T, Dellart F. "An MCMC-based particle filter for tracking multiple interacting targets." *Computer Vision-ECCV* 2004 3024: 279-290. 2004; the disclosure of which is herein incorporated by reference in its entirety). The JPDAF and particle filters are discussed in more detail in the "Algorithm Descriptions" section.

CalculateMetrics(allCells)
a. Input: A set of all cell objects
b. Output: A feature vector summarizing the sample
c. Description: Once the cell tracks have been satisfactorily established, the next system may calculate metrics from the cells at one or more different levels such as: individual, full-population aggregate, and aggregate of interesting sub-populations. Individual metrics can include: net distance travelled, displacement, and means/variances of velocity, orientation, circularity, area, and momentum (as well as second derivatives of certain of these metrics). Aggregate metrics, both for full-population and select sub-populations, may be calculated as averages across the previously mentioned individual metrics for the relevant set of cells. LISTING 5 gives example pseudocode for calculating a mean speed metric (by cell and by frame).

LISTING 5

```
CalculateMetrics_JustSpeed(allCells)
        featureVector ←•Ø
        cellSpeedAccumulator ←•Ø
        for cell in allCells do
                cellSpeedSum ←•0
                for i in 1:videoFrames.size( ) do
                     cellSpeedSum ←•cellSpeedSum +...
                             Sqrt((cell.positionAt(i) −...
                             cell.positionAt(i − 1)²)
                end
                cellMeanSpeed ←•cellSpeedSum / videoFrames.size( )
                cellSpeedAccumulator.add(cellMeanSpeed)
        end
        frameSpeedAccumulator ←•Ø
        for i in 1:videoFrames.size( ) do
                frameSpeedSum ←•0
                for cell in allCells.cellsInFrame(i) do
                    frameSpeedSum ←•frameSpeedSum +...
                             Sqrt((cell.positionAt(i) −...
                             cell.positionAt (i − 1)²)
                end
                frameMeanSpeed ←•frameSpeedSum /...
                             allCells.cellsInFrame(i).size( )
                frameSpeedAccumulator.add(frameMeanSpeed)
        end
        featureVector.add(Mean(cellSpeedAccumulator))
        featureVector.add(Mean(frameSpeedAccumulator))
        return featureVector
```

In some implementations, all of these metrics may be calculated concurrently. Note that the output of this function is a feature vector. Use of a feature vector allows encoding of all of the information in a manner that can be used for sample classification via machine learning techniques.

Classify(featureVector)
a. Input: A feature vector
b. Output: The patient's inflammatory index
c. Description: This function may take the feature vector from the previous module as an input. The feature vector may be used to classify a sample (e.g., a patient's blood sample), using machine learning techniques to calculate the patient's inflammatory index based on a database of similar feature vectors from previous blood samples. A decision tree-based approach may be implemented to classify the sample. Alternative or additional machine learning methods may be included for classification, such as: k-nearest neighbor classification, k-means clustering, and support vector machines. This evaluation may be done using the Weka machine learning software suite from the University of Waikato, New Zealand. Weka makes it easy to train and test classifiers using different machine learning methods with minimal effort on the user's part. Details on these algorithms are provided in the following section. For further details on Weka's specific implementations, refer to the developers' textbook (Hall M A, Witten I, and Frank E. "Data mining: Practical machine learning tools and techniques." *Kaufman, Burlington.* 2011; the disclosure of which is herein incorporated by reference in its entirety). LISTING 6 shows an example high-level pseudocode implementation using a decision tree's rules to classify a feature vector.

LISTING 6

```
Classify(featureVector)
    node ←•DecisionTree.root
        while true
            if featureVector.valueX > node.valueThreshold do
        newNode ←•node.childA
            else
        newNode ←•node.childB
            end
            if newNode = terminalNode do
        break
            else
                node ←•newNode
                continue
            end
        end
        inflammatoryIndex ←•terminalNode.classification
        return inflammatoryIndex
```

Algorithm Descriptions

Foreground extraction: While this is itself quite a broad term encompassing a wide range of approaches in the literature, extracting the foreground (e.g., portion of the image showing cells) in each frame may include three steps: finding pixels with high variance (both temporal and from the image mean pixel value), converting the image to a binary representation by thresholding pixels based on their variance, and extracting the blobs that represent the connected components in the binary image.

a. Variance calculation: To calculate temporal variance, each pixel in the image may be compared to pixel values at the same image coordinate for m frames before and after the current frame (where m is a parameter that can be tuned experimentally), and the variance of the pixel in that window may be calculated. The variance from the image mean may be a pseudo-variance: the difference is found between each individual pixel and the image mean value, and then these values are squared. These two variance values can be combined to produce a single variance value for each pixel, with some mixing proportion $0<\theta<1$ (see, e.g., LISTING 3).

b. Thresholding by variance: A threshold may be determined for each frame based on the mean and standard deviation of the variance values calculated in the previous step. The threshold can be defined as this mean plus n standard deviations (where n is an experimentally-tunable parameter). Pixels with variance values above the threshold may be kept as foreground (e.g., given a value of 1), while pixels below the threshold variance level may be rejected as foreground (e.g., given a value of 0 and thus corresponding to background pixels).

c. Blob extraction: connected components in the binary image may be found ("blobs" of pixels with value 1), which denote likely cell locations. Blob extraction may include processing using a computer vision library such as the OpenCV computer vision library, and its "findContours" function. Each contour (which is just the outline of a blob) represents a foreground object, which may be a cell. As an extra step, contours of blobs that are too big or too small for the cells to be detected may be removed from the set of contours that is returned by the algorithm.

Cell Tracking

Joint probability data association filter (JPDAF): When attempting to track multiple targets (in this case, cells) in a cluttered environment, there can be some uncertainty as to exactly which detected object in frame n corresponds to which detected object in frame n+1. Additionally, certain objects may be missed in some frames, and some object "detections" will be generated by clutter. The JPDAF may be implemented in whole or in part using an algorithm designed to take this scenario and calculate the highest probability data association for tracking multiple targets through clutter. In each frame, every detection may be assigned a probability of having been generated by each known target. These probabilities can be informed by predictions about the object's movement between frames, which may be generated by a particle filter. At the end of the process, all targets may be assigned to detections in such as way that the probability of all associations is maximized through the entire video.

Particle filters: A particle filter uses known information about the position of a tracked object and how it is expected to move in the next time step to predict the likeliest location of the same object in the next frame. In each time step, the particle filter may use its expected motion model for the target to generate a set of n hypotheses (called particles) for the location of the target in the next frame (where n is a tunable parameter). Each of these particles can be weighted based on, for example, a scoring function that evaluates how likely the particle is to be the true location of the object based on the pixel values in the next frame. Particles with greater weight are more likely to be propagated into future frames, while unlikely particles die out. Though most filtering algorithms generate object state predictions may have lower computational complexity, they tend to be limited in accuracy to cases where the target's motion is expected to be linear, or at least linearly approximable. The particle filter, being somewhat probabilistic, does not suffer from this same constraint, sacrificing some computational efficiency for greater applicability.

Machine Learning

Decision trees: Decision trees approach the classification problem by splitting the search space based on the most influential features in the feature vector. The training algorithm may generate a set of rules of the form "if attribute x is greater than value y, then evaluate rule z; else evaluate rule w". Each path down the tree can terminate in a classification for the feature vector being evaluated. It may be desirable to generate a decision tree having many short paths between rules. The most influential rules may be organized near the root of the tree. For added specificity, decision trees may be combined in methods such as a random forest; which uses the combination of multiple decision trees to help avoid overfitting the classifier to training data (Hall M A, Witten I, and Frank E. "Data mining: Practical machine learning tools and techniques." Kaufman, Burlington. 2011; the disclosure of which is herein incorporated by reference in its entirety).

K-means clustering: Each data point from the training set of data can be encoded as a feature vector. All of these vectors may be mapped into n-dimensional space, where n is the number of features in the feature vector. The system may cluster these points into k clusters, where k is a tunable parameter (e.g., based on a configuration, detected value, cell of interest, sample type, etc.). The calculation to find these clusters may include an iterative process, where 'guesses' are refined over each iteration until a maximum number of iterations is reached, or until the clusters converge to k locations and cease changing between iterations. Each cluster can be viewed as a different label for the data; for example, in the implementation at hand, each cluster could refer to a different level of inflammation.

K-nearest neighbor classification: The system assumes that all of the training data has been labeled (e.g. data point 1 has low inflammation, data point 2 has medium inflammation, etc.) prior to performing k-nearest neighbor classification. This can either be done by hand, or by the system such as via a clustering algorithm. When a new data point is collected, it may be mapped into the same n-dimensional space as the training data, and its Euclidean distance from each other point is calculated. The k points closest to the new point may be found, and the new point is given the label that occurs most frequently in these k nearest neighbors.

Expectation-maximization (EM): This algorithm functions quite similarly to the k-means clustering method, but leads to more probabilistic results. Each data point is not assigned to just one cluster, but is given a probability value for each cluster that the point belongs to that cluster (with all probabilities summing to 1). This algorithm can alternate between an E-step (expectation), in which each point is assigned its probabilities associated with each cluster; and an M-step (maximization), in which the parameters of the clusters (e.g. mean and variance) are altered to maximize the location of the clusters given these probabilities. These steps may be repeated for a maximum number of iterations, or until the algorithm converges. When a new data point is collected, it may be evaluated using the same function that assigns each training point its probability of being in each cluster. The cluster for which the new point has the highest probability may be returned as its label.

Support vector machines: In systems that include support vector machines, data is preferably labeled before processing. Once data is plotted as feature vectors into the n-dimensional feature space, boundaries can be calculated that lead to the greatest separation between labels. Any new data points that are mapped into this space will fall within some region defined by these boundaries and receive the classification of that region.

Additional Image Processing Applications

In addition to serving as the quantifying component of the method for assessing immune activity, this disclosed image processing features may additionally prove valuable in the context of other biological needs in both clinical and research settings. These additional applications include the automated measurement and statistical analysis of still-frame microscopy images, such as those produced for histological analysis or those used for cell characterization experiments. The image processing methods described would also be suitable for the automated analysis video-based assays that are currently assessed manually, namely migratory glial cell assays and clinical sperm viability assays. Repurposing the system to suit the specific needs of these alternate utilizations would entail only minor alterations to enforced detection parameters and result calibration to match specific systems.

Example Method of Image Processing

Figure 9:
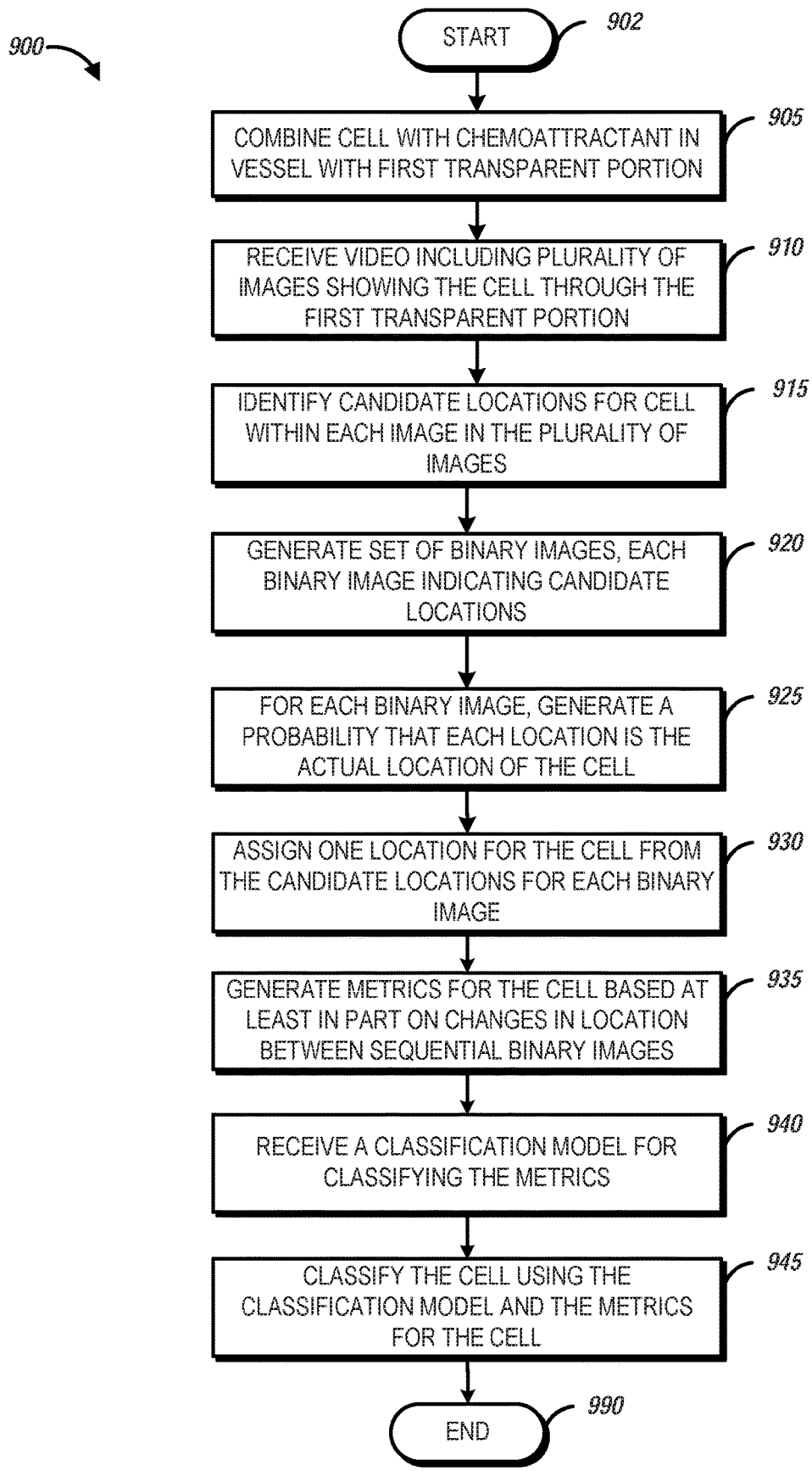
FIG. 9 is a flow diagram showing an illustrative method of image processing.

FIG. 9 is a flow diagram showing an illustrative method of image processing. The method 900 shown in FIG. 9 may be implemented in whole or in part by one or more of the devices described herein such as the image processing system 812 or the microscope 804. The method 900 includes features to classify a cell based on a series of images showing the cell where the series of images are captured over a period of time. The features may include one or more of the image processing features described in conjunction with LISTINGS 1, 2, 3, 4, 5, and/or 6.

The method 900 begins at block 902. At block 905, the cell is combined with a chemoattractant in a vessel having a first transparent portion. The vessel may be a chemotaxis cassette such as those described herein.

At block 910, video including a plurality of images shown the cell through the first transparent portion is received by the device(s) implementing the method 900. Each image may be associated with a sequence number to facilitate ordering the images according to the sequence in which they were captured. In some implementations, the sequence may be inferred based on time information included with the image. The video may include at least 180 images and show 100, 200, 299, or more cells.

At block 915, for each image included in the video, a set of locations within an image where the cell may be located is identified. The identification is performed using at least one of temporal variance in pixel values between images and pixel variance from a mean for the image.

At block 920, a binary image for the image is generated. The binary image indicates the set of locations where the cell may be located. For example, a pixel may be turned on (e.g., black) if the cell may be located at the location while a pixel may be turned off (e.g., white) if the cell is not believed to be located at the location. In some instances, the binary image may require fewer resources (e.g., memory, processor instructions, bandwidth, etc.) to store and process than the original image from the video.

At block 925, for each binary image, a probability that each location identified as a possible location in the binary image is the actual location of the cell. The method 900 may include determining a hypothesis count based on at least one of a type for the cell and the chemoattractant and obtaining a motion model for the cell. The motion model may receive at least a location of the cell in a first image as an input and generating a predicted location for the cell in a subsequent image as an output. In some implementations, the method 900 may include, for each binary image, generating a set of hypothetical locations for the cell using the motion model, wherein the size of the set of hypothetical locations corresponds to the hypothesis count. The method 900 may then assign a score to each hypothetical location in the set of hypothetical locations based on a similarity calculated using a negative exponential Gaussian function of the Mean Squared Error (MSE) between the hypothetical location and a template image, wherein the probability that each location in the set of locations is the location of the cell is generated using the scores.

At block 930, one location is assigned as the location for the cell. The location may be the location having the highest probability for all the binary images. Accordingly, the assignment of one binary image affects the possible location in subsequent binary images. Each location, in turn, is associated with a probability. At block 930, the method 900 finds an optimal location that, in the example shown in FIG. 9, maximized the probability.

At block 935, one or more metric for the cell may be generated. A metric may indicate a metric indicating a characteristic of the cell shown in the image included in the plurality of images sequentially captured. A metric may indicate a change in a characteristic of the cell between images included in the plurality of images sequentially captured. For example, the characteristic of the cell may be: cell area, cell velocity, direction of cell migration, cell speed, cell momentum, cell polarization, cell circularity, number of distinct protrusions from each cell, and/or any first order time-dependent derivatives thereof.

At block 940, a classification model may be received. The classification model may receive the metrics generated at block 935 and provide a classification of the cell. The classification may provide an inflammatory index for the cell associated with the provided set of metrics. At block 945, the specific metrics for a cell are classified using the classification model. The classification may be provided for display or further processing (e.g., additional analysis, storage, on-demand printing system, etc.). The method 900 ends at block 990.

Hardware and Operating System

The above-described algorithms for image processing and analysis, for training and testing classifiers, and for using classifiers can be implemented in source code using a variety of languages, and in preferred implementations may be written using C++ for improved execution speed. The source code will generally be compiled into object code, which is stored on a memory and then executed on a processor at runtime. Any suitable computing environment having a memory and a processor can be used, and preferred implementations may use a Lenovo ThinkPad X201 with a 2.4 GHz Intel Core i5 processor, 4 GB of memory, and a 750 GB hard drive. The computing environment may have an operating system, such as Ubuntu 14.04. Both the image processing software and the software for training, testing and using classifiers can run successfully in such an environment. However, alternative implementations may use alternative operating systems such as Mac OS X, for which the image processing software and the software for training, testing and using classifiers are also suitable. The data sets used for the training and testing classifiers and the data sets against which the patient data is classified may be stored in a memory, either locally or on a memory of a remote server.

The terms "processor" and "processor module," as used herein are a broad terms, and are to be given their ordinary and customary meaning to a person of ordinary skill in the art (and are not to be limited to a special or customized meaning), and refer without limitation to a computer system, state machine, processor, or the like designed to perform arithmetic or logic operations using logic circuitry that responds to and processes the basic instructions that drive a computer. In some embodiments, the terms can include ROM and/or RAM associated therewith.

As used herein, the term "determining" encompasses a wide variety of actions. For example, "determining" may include calculating, computing, processing, deriving, investigating, looking up (for example, looking up in a table, a database or another data structure), ascertaining and the like. Also, "determining" may include receiving (for example, receiving information), accessing (for example, accessing data in a memory) and the like. Also, "determining" may include resolving, selecting, choosing, establishing, and the like.

As used herein, the term "message" encompasses a wide variety of formats for representing information for transmission. A message may include a machine readable aggregation of information such as an XML document, fixed field message, comma separated message, or the like. While recited in the singular, it will be understood that a message may be composed/transmitted/stored/received/etc. in multiple parts.

As used herein "generate" or "generating" may include specific algorithms for creating information based on or using other input information. Generating may include retrieving the input information such as from memory or as provided input parameters to the hardware performing the generating. Once obtained, the generating may include combining the input information. The combination may be performed through specific circuitry configured to provide an output indicating the result of the generating. The combination may be dynamically performed such as through dynamic selection of execution paths based on, for example, the input information, device operational characteristics (e.g., hardware resources available, power level, power source, memory levels, network connectivity, bandwidth, and the like). Generating may also include storing the generated information in a memory location. The memory location may be identified as part of the request message that initiates the generating. In some implementations, the generating may return location information identifying where the generated information can be accessed. The location information may include a memory location, network locate, file system location, or the like.

As used herein "receive" or "receiving" may include specific algorithms for obtaining information. For example, receiving may include transmitting a request message for the information. The request message may be transmitted via a network as described above. The request message may be transmitted according to one or more well-defined, machine readable standards which are known in the art. The request message may be stateful in which case the requesting device and the device to which the request was transmitted maintain a state between requests. The request message may be a stateless request in which case the state information for the request is contained within the messages exchanged between the requesting device and the device serving the request. One example of such state information includes a unique token that can be generated by either the requesting or serving device and included in messages exchanged. For example, the response message may include the state information to indicate what request message caused the serving device to transmit the response message.

As used herein a "user interface" (also referred to as an interactive user interface, a graphical user interface or a UI) may refer to a network based interface including data fields and/or other controls for receiving input signals or providing electronic information and/or for providing information to the user in response to any received input signals. A UI may be implemented in whole or in part using technologies such as hyper-text mark-up language (HTML), Flash, Java, .net, web services, and rich site summary (RSS). In some implementations, a UI may be included in a stand-alone client (for example, thick client, fat client) configured to communicate (e.g., send or receive data) in accordance with one or more of the aspects described.

The various illustrative logical blocks, modules, circuits, pseudocode, and algorithm steps described in connection with the embodiments disclosed herein can be implemented as electronic hardware, computer software, or combinations of both. To clearly illustrate this interchangeability of hardware and software, various illustrative components, blocks, modules, circuits, pseudocode, and steps have been described above generally in terms of their functionality. Whether such functionality is implemented as hardware or software depends upon the particular application and design constraints imposed on the overall system. The described functionality can be implemented in varying ways for each particular application, but such embodiment decisions should not be interpreted as causing a departure from the scope of the disclosure.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

EXAMPLES

Experiment Background

From December of 2014 through March of 2015, a clinical study was conducted using human samples. This study utilized the technology detailed in this document to assess and monitor patient inflammation and compare results to those of industry standards. Ten volunteer patients scheduled to undergo surgical procedures, specifically catheter ablation, were selected for monitoring. Catheter ablation is a procedure used to treat certain kinds of atrial fibrillation by means of destroying small areas of heart tissue that contribute to arrhythmia. This operation is considered a preferable treatment option for arrhythmia in many cases and patients are typically discharged from hospital care within 24 hours of the operation (Terasawa T, Balk E M, et al. "Systematic Review: Comparative Effectiveness of Radiofrequency Catheter Ablation for Atrial Fibrillation." *Annals of Internal Medicine* 151(3): 191-202). This surgical model provides a suitable opportunity to track dynamic changes in human immune response over the course of an inflammation-inducing event. For this study, patients were predicted to demonstrate immune activity typical of non-symptomatic phenotypes prior to surgery (i.e. baseline), exhibit elevated immune activity levels following surgery (i.e. inflammation), and return to baseline activity levels over the course of recovery. Platform performance was therefore evaluated by its ability to match these anticipated results. To mitigate confounding factors that might contribute to heightened immune response, patients with histories of inflammation-mediated disease or with signs of infection were excluded from the study.

Experiment Design

Samples were collected from each of the 10 enrolled patients at four separate time points over the course of surgery and recovery: once immediately prior to undergoing catheter ablation, once the following morning prior to hospital. All samples were drawn by certified professionals and promptly transferred for processing and analysis. Granulocytes were manually retrieved from patient blood samples using the density-mediated isolation protocol described earlier in this document. Following immune cell isolation, samples were introduced to cassettes and allowed to adhere the channel surface. The channel was then filled, an fMLF chemogradient was produced, and biophysical cell activity was tracked using phase-contrast microscopy and time-lapse videography. If time and sample availability were sufficient, duplicate assays were run for each sample and the population results of each run were averaged. Assays were conducted for a duration of 30 minutes, capturing one picture every 10 seconds (180 frames total).

Each resulting patient video was analyzed using custom software described above. Computer vision techniques were employed to follow the crawling path of each relevant cell tracked and biophysical characteristics of interest were measured for each frame. Collected measurements for each cell were then combined into single outputs, creating an average value of each metric for each detected cell. These average cell values were then averaged at the population level, giving a single value for each measured biophysical characteristic. Finally, these population-level metrics were weighted in accord to their perceived significance to the process of immune activity, resulting in a single readout value dubbed the inflammatory index.

At the time of each sample acquisition, additional blood samples were taken for the purpose of running C-reactive protein (CRP) tests. These tests were run by medical professionals and resulting values were reported to. Additionally, case report files for each patient detailing recent medical history were provided.

Monitoring of Disease State Over Time

The systems, devices, and methods detailed herein can be utilized for the purpose of monitoring immune response in a patient over a given length of time in order to assess any notable changes or lack thereof. This could be applied, for instance, to gauge the efficacy of anti-inflammatory therapies in patients with autoimmune disorders or of immunotherapies in cancer patients. This would help to inform in a more direct and timely manner whether medications are working as intended and how well chronic disease states are being managed. Additionally, this application provides the possibility of immediate clinical feedback in cases where care is highly time-sensitive, as is the case with infectious disease. Longitudinal disease monitoring with the systems, devices, and methods described may prove particularly useful in cases of chronic lung diseases (asthma, COPD), autoimmune disorders (arthritis, lupus, IBD, etc.), infectious disease (sepsis, meningitis, etc.), and cancer.

Highlighting Suitable Candidates for Therapeutic Regimens

One additional clinical application for the immunophenotyping systems, devices, and methods described is to use single-point assessment to match patients with medications most likely to have the greatest effect. Using a database of known immune profiles and disease states, it is possible to match a patient to a good therapeutic candidate based on what has been known to work in other patients exhibiting similar phenotypes. This, for instance, would be applicable in cases of cancer in which immunotherapy is an available option. It is currently difficult to predict in advance which patients will best respond to immunotherapy and which will experience severe adverse outcomes. Using this method of immune profile matching, however, it may be possible to predict with a high degree of accuracy whether a patient will be best served by immunotherapy or by a more traditional regimen. Likewise, this methodology could be used to match patients with inflammation-mediated disease to anti-inflammatories, superseding the need for a guess-and-check approach.

Prediction of Disease Exacerbation or Progression

In cases of chronic inflammation-mediated diseases characterized by spontaneous states of acute exacerbation, such as asthma and COPD, the systems, devices, and methods described may be used to predict acute events prior to the onset or worsening of symptoms. In patient populations where the avoidance of such events is critical, regular (e.g. weekly) use of this technology may be used to track inflammatory response over time. In certain cases, this would allow clinicians to identify acute inflammatory events as early as possible and begin therapies for the treatment of the identified event or disease. Additionally, inflammation tracking would allow clinicians to more easily identify gradual worsening of patient health and respond accordingly.

Disease-Specific Diagnostics

This platform may also be used to direct clinical diagnostic efforts in cases where symptoms might be attributed to multiple causes. This is a particularly valuable application because many inflammation-mediated conditions are symptomatically similar but require very different therapeutic regimens for proper management. For example, if a patient were to come to a physician with complaints of vague symptoms, the technology described here may be used as a point-of-care diagnostic to compare that patient's immune profile against a database of other known profiles correlated to condition and produce a likely cause of symptoms (e.g. lupus). In another setting, this application may be used to differentiate inflammation brought on by infection, making the platform highly suitable as an early detector of sepsis. This case example could apply to any disease state that shows to have a signature effect on human immune function.

Results

For every patient tested monitored by the platform, immune activity levels were demonstrated to rise from baseline measurements following surgery and to return to lower activity levels by the final time point. In 9 of 10 tested patients, inflammation levels were highest in samples collected soon following surgery, and a decrease in overall presence of inflammation is detected thereafter (FIG. 5). These findings highly correlated with study expectations and demonstrate that the platform can sensitively assess immune response by means of live cell behavior. Conversely, the CRP test was found to exhibit more erratic results, detecting peak immune activity levels several days following surgery in some patients, or detecting little to no change at all in other patients such as shown in FIG. 4.

This study provided concrete evidence supporting the efficacy of the proposed technology in a clinical setting. Further, this study evidenced clinical superiority of the proposed technology over a current industry standard for gauging patient immune response, namely the CRP test. In all, the technology proposed herein greatly outperformed industry standards for gauging real-time immune response, validating the platform as a useful and uniquely capable tool for clinical application.

The features described may be applicable to fields other than diagnostics. For example, aspects may be applied for image/video-based analysis of effector cells (primarily immune cells such as T cell, NK cells, etc.) interactions with target cell populations (e.g., tumor cells) measuring killing potential of effector cells after stimulations with experimental therapeutics or other stimuli in pre-clinical in vitro assays for helping identify most promising therapeutics for further development. As another example, aspects may be included for image/video-based analysis of changes in cell (primarily stem cell) populations over the course of culture/differentiation (bioprocessing) and utilizing machine-learning methodologies to build both predictive models of optimal differentiation conditions as well as quality control models for assessing batch quality at various time points over course of production to determine if batch is worth continuing to produce or not. Certain image processing features may be included for image-based analysis for imaging flow cytometry to extract more features from cells than currently captured and building accompanying machine-learning models to correlate to signatures of unique cell populations for rare cell population identification and for creating templates to guide fluorescence-activated cell sorter (FACS) to sort cells. A further area in which the features described may be employed is image/video-based analysis of central nervous system (CNS) based immune cells migrating to multiple target cell populations (e.g., endothelial cells, astrocytes, neuronal cells, etc.) in pre-clinical in-vitro assays under varying stimulations to identify which pathways drive preferential migration to specific target cell populations and identifying potential therapeutics that modulate these behaviors for further development.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, thebare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system for classifying a cell, the system comprising:
   a sample vessel including:
      a sample reservoir configured to receive a sample and said sample reservoir comprising one or more cell adhesion molecules and a chemoattractant for an assay;
      an elongate channel; and
      a processing chamber in fluid communication with the sample reservoir through the elongate channel;
   an imaging device configured to capture images of the processing chamber;
   a control server configured to adjust the imaging device based at last in part on the assay; and
   an image processing system configured to:
      receive the images, wherein each image shows the cell, wherein a plurality of images generates a video;
      generate a binary image for each image included in the images, individual binary image indicating a set of locations within the respective image where the cell may be located; and
      for each binary image:
         generate a probability that each location in the set of locations is the location of the cell;
         assign one location from the set of locations for each binary image, the assignment maximizing the probability for all of the binary images;
         generate a set of metrics for the cell, the set of metrics generated using changes in a characteristic for the cell between binary images for sequentially captured images included in the video; and
         classify the cell using the set of metrics and a classification model, the classification model receiving at least a portion of the set of metrics as an input and generating a classification as an output.

2. A method of classifying a cell, the method comprising:
   combining the cell with a chemoattractant in a vessel having a first transparent portion;
   receiving a video including a plurality of images showing the cell through the first transparent portion; and
   for each image included in the plurality of images:
      identifying a set of locations within an image where the cell may be located using at least one of temporal variance in pixel values between images and pixel variance from a mean for the image, and
      generating a binary image for the image, the binary image indicating the set of locations;
   for each binary image:
      generating a probability that each location in the set of locations is the location of the cell;
      assigning one location from the set of locations for each binary image, the assignment maximizing the probability for all of the binary images;
      generating a set of metrics for the cell, the set of metrics generated using changes in location for the cell between binary images for sequentially captured images included in the video;
      obtaining a classification model, the classification model receiving at least a portion of the set of metrics as an input and generating a classification as an output; and
      classifying the cell using the set of metrics and the classification model.

3. The method of claim 2, further comprising:
   determining a hypothesis count based on at least one of a type for the cell and the chemoattractant;
   obtaining a motion model for the cell, the motion model receiving at least a location of the cell in a first image as an input and generating a predicted location for the cell in a subsequent image as an output; and
   for each binary image:
   generating a set of hypothetical locations for the cell using the motion model, wherein the size of the set of hypothetical locations corresponds to the hypothesis count, and
      assigning a score to each hypothetical location in the set of hypothetical locations based on a similarity calculated using a negative exponential Gaussian function of the Mean Squared Error (MSE) between the hypothetical location and a template image, wherein the probability that each location in the set of locations is the location of the cell is generated using the scores.

4. The method of claim 2, further comprising:
   generating a random seed value for generating the probability for each location in the set of locations for each binary image;
   storing the random seed value in a data storage device in association with an identifier for a source of the cell;
   receiving a second video including a plurality of images showing a second cell from the source;
   extracting a portion of an image included in the plurality of images, the portion indicating the identifier;
   retrieving the random seed value from the data storage device using the identifier; and
   classifying the second cell using the random seed value.

5. The method of claim 2, wherein the set of metrics includes a metric indicating a characteristic of the cell shown in the image included in the plurality of images sequentially captured.

6. The method of claim 2, wherein the set of metrics includes a metric indicating a change in a characteristic of the cell between images included in the plurality of images sequentially captured.

7. The method of claim 6, wherein the characteristic of the cell comprises cell area, cell velocity, direction of cell migration, cell speed, cell momentum, cell polarization, cell circularity, number of distinct protrusions from each cell, and all first order time-dependent derivatives thereof.

8. The method of claim 2, wherein the plurality of images comprises at least 180 images, and wherein each of the plurality of images further show between 1 and 299 other cells through the first transparent portion.

9. The method of claim 2, wherein the chemoattractant comprises N-Formylmethionyl-leucyl-phenylalanine (fMLF), fMet, IL-8, Leukotrene B4, CXCL1, CXCL2, CXCL8, CXCL9, CXCL10, CXCL12, CCL2, CCL3, CCL5, CCL11, CCL19, CCL21, CX3CL1, C5a, C5b, G-CSF, GM-CSF, IL-1, IL-3, IL-4 IL-5, IL-6, IL-7, IL-11 IL-17, IL-21, IL-1β, TNFα, stem cell factor (SCF), thrombin, erythropoietin (EPO), IFN-α, IFN-β, IFN-γ and any combination thereof.

10. The method of claim 2, further comprising:
providing a device for measuring an inflammatory response in a subject, the device including:
a sample reservoir having one or more cell adhesion molecules and a chemoattractant, and
a processing chamber in fluid communication with the sample reservoir through an elongate channel; and
applying a biological sample to the sample reservoir, the biological sample comprising one or more cells, and the one or more cells including the cell.

11. A non-transitory computer-readable medium comprising instructions that, when executed by at least one processor of a computing device, cause the computing device to:
receive a video including a plurality of images showing the cell through the first transparent portion; and
for each image included in the plurality of images:
identify a set of locations within an image where the cell may be located using at least one of temporal variance in pixel values between images and pixel variance from a mean for the image, and
generate a binary image for the image, the binary image indicating the set of locations; and
for each binary image:
generate a probability that each location in the set of locations is the location of the cell;
assign one location from the set of locations for each binary image, wherein the assignment maximizes the probability for all of the binary images;
generate a set of metrics for the cell, the set of metrics generated using changes in location for the cell between binary images for sequentially captured images included in the video;
obtain a classification model, the classification model receiving at least a portion of the set of metrics as an input and generating a classification as an output; and
classify the cell using the set of metrics and the classification model.

12. A method of classifying a cell, the method comprising:
receiving a video including a plurality of images showing the cell;
generating a binary image for each image included in the plurality of images, individual binary image indicating a set of locations within the respective image where the cell may be located; and
for each binary image:
generating a probability that each location in the set of locations is the location of the cell;
assigning one location from the set of locations for each binary image, the assignment maximizing the probability for all of the binary images;
generating a set of metrics for the cell, the set of metrics generated using changes in a characteristic for the cell between binary images for sequentially captured images included in the video; and
classifying the cell using the set of metrics and a classification model, the classification model receiving at least a portion of the set of metrics as an input and generating a classification as an output.

13. The system of claim 1, wherein the one or more cell adhesion molecules is a lectin, a laminin, a selectin, a fibronectin, a collagen, a fibrinogen, or a gelatin.

14. The system of claim 1, wherein the chemoattractant is N-Formylmethionyl-leucyl-phenylalanine (fMLF), fMet, IL-8, Leukotrene B4, CXCL1, CXCL2, CXCL8, CXCL9, CXCL10, CXCL12, CCL2, CCL3, CCL5, CCL11, CCL19, CCL21, CX3CL1, C5a, C5b, G-CSF, GM-CSF, IL-1, IL-3, IL-4 IL-5, IL-6, IL-7, IL-11 IL-17, IL-21, IL-1β, TNFα, stem cell factor (SCF), thrombin, erythropoietin (EPO), IFN-α, IFN-β, or IFN-γ.

15. The system of claim 1, wherein the imaging device is a camera configured to capture magnified images of the processing chamber.

16. The system of claim 1, wherein the set of metrics includes a metric indicating a change in a characteristic of the cell between images included in the plurality of images sequentially captured.

17. The computer readable medium of claim 11, wherein a probability that each location in the set of locations is the location of the cell is generated using a score.

18. The computer readable medium of claim 11, wherein the set of metrics includes a metric indicating a change in a characteristic of the cell between images included in the plurality of images.

19. The computer readable medium of claim 11, wherein the cell is classified by assessing one or more physical variables of the cell.

20. The computer readable medium of claim 19, wherein the one or more physical variables include cell morphology, cell position, cell directionality, cell orientation, cell perimeter, cell luminance, cell area, cell velocity, cell speed, cell acceleration, cell direction, cell circularity, cellular branching events, cell branch length, cell image moments (or Hu moments), cell eccentricity, cell path trends, cell spreading, cell grouping, neutrophil extracellular trap (NET) formations, degranulation events, or overall prevalence.

21. The method of claim 12, wherein the set of metrics includes a metric indicating a change in a characteristic of the cell between images included in the plurality of images.

22. The method of claim 12, wherein the cell is classified by assessing one or more physical variables of the cell.

23. The method of claim 22, wherein the one or more physical variables include cell morphology, cell position, cell directionality, cell orientation, cell perimeter, cell luminance, cell area, cell velocity, cell speed, cell acceleration, cell direction, cell circularity, cellular branching events, cell branch length, cell image moments (or Hu moments), cell eccentricity, cell path trends, cell spreading, cell grouping, neutrophil extracellular trap (NET) formations, degranulation events, or overall prevalence.

24. The method of claim 12, wherein the plurality of images comprises at least 180 images.

* * * * *